US009409988B2

(12) United States Patent
Robert et al.

(10) Patent No.: US 9,409,988 B2
(45) Date of Patent: Aug. 9, 2016

(54) ANTI-AXL ANTIBODIES AND USES THEREOF

(75) Inventors: Bruno Robert, Montpellier (FR); Benedicte Fauvel, Montpellier (FR); Gwenael Cheve, Montpellier (FR); Aziz Yasri, Montpellier (FR); Christel Larbouret, Montpellier (FR); Wilhem Leconet, Montpellier (FR); Thierry Chardes, Montpellier (FR); Christian Larroque, Montpellier (FR); Andre Pelegrin, Montpellier (FR)

(73) Assignees: INSERM (Institut National De La Sante Et De La Recherche Medicale) (FR); ORIBASE Pharma (FR); UNIVERSITE De Montpellier 1 (FR); INSTITUT Regional Du Cancer De Montpellier-Val D'Aurelle (FR)

( * ) Notice: Subject to any disclaimer, the term of this patent is extended or adjusted under 35 U.S.C. 154(b) by 0 days.

(21) Appl. No.: 14/127,416

(22) PCT Filed: Jun. 22, 2012

(86) PCT No.: PCT/EP2012/062115
§ 371 (c)(1),
(2), (4) Date: Apr. 24, 2014

(87) PCT Pub. No.: WO2012/175692
PCT Pub. Date: Dec. 27, 2012

(65) Prior Publication Data
US 2014/0227283 A1    Aug. 14, 2014

Related U.S. Application Data

(60) Provisional application No. 61/504,256, filed on Jul. 4, 2011.

(30) Foreign Application Priority Data

Jun. 22, 2011 (EP) .................................... 11305792

(51) Int. Cl.
| C07K 16/40 | (2006.01) |
| C07K 16/28 | (2006.01) |
| C07K 16/32 | (2006.01) |
| G01N 33/574 | (2006.01) |
| G01N 33/68 | (2006.01) |
| A61K 39/00 | (2006.01) |

(52) U.S. Cl.
CPC ............. *C07K 16/28* (2013.01); *C07K 16/32* (2013.01); *G01N 33/57492* (2013.01); *G01N 33/6872* (2013.01); *A61K 2039/505* (2013.01); *C07K 2317/33* (2013.01); *C07K 2317/34* (2013.01); *C07K 2317/565* (2013.01); *C07K 2317/73* (2013.01); *C07K 2317/76* (2013.01); *C07K 2317/92* (2013.01)

(58) Field of Classification Search
CPC .......................................... C07K 16/00–16/468
See application file for complete search history.

(56) References Cited

U.S. PATENT DOCUMENTS

| 2012/0014870 A1* | 1/2012 | Aburatani | ............ | C07K 5/1008 |
| | | | | 424/1.49 |
| 2014/0302041 A1* | 10/2014 | Robert | ............... | C07K 16/2863 |
| | | | | 424/139.1 |

FOREIGN PATENT DOCUMENTS

| EP | 1 382 969 | 1/2004 |
| EP | 2 228 392 | 9/2010 |
| EP | 2 270 053 | 1/2011 |
| EP | 2 270 053 A1 | 1/2011 |
| WO | 2009/062690 | 5/2009 |
| WO | 2009/063965 | 5/2009 |
| WO | WO2009/062690 A1 * | 5/2009 |
| WO | 2010/131733 | 11/2010 |
| WO | 2011/014457 | 2/2011 |

OTHER PUBLICATIONS

Chan and Carter, Nature Reviews Immunology, 2010; 10:301-316.*
Li et al., Oncogene 2009; 28:3442-55.*
Lemke and Rothlin, Nat. Rev. Immunol. 2008; 8:327-36.*
V.A. Korshunov, Clin. Sci. 2012; 122:361-68.*
Brand et al., Arthritis Rheum., 2013; 65:671-80.*
Brindley et al., Virology. 2011; 415:83-94.*
Bartolazzi et al., The Lancet 2008; 9:543-49.*
Verma et al., Mol. Cancer Therapeutics 2011; 10(10):1763-73.*
E. A. Padlan, Adv Prot Chem 49:57-133; 1996.*
Corada et al., Blood, 2001; 97:1679-84.*

* cited by examiner

*Primary Examiner* — Jessica H Roark
(74) *Attorney, Agent, or Firm* — McAndrews, Held & Malloy, Ltd.

(57) ABSTRACT

The present invention relates to anti-Axl antibodies and uses thereof in diagnostic and therapeutic methods. More particularly, the present invention relates to a monoclonal antibody having specificity for Axl comprising an heavy chain variable region comprising SEQ ID NO:2 in the H-CDR1 region, SEQ ID NO:3 in the H-CDR2 region and SEQ ID NO:4 in the H-CDR3 region; and a light chain variable region comprising SEQ ID NO: 6 in the L-CDR1 region, SEQ ID NO:7 in the L-CDR2 region and SEQ ID NO:8 in the L-CDR3 region. Said monoclonal antibody binds to the extracellular domain of Axl via, SEQ ID NO:9 and SEQ ID NO: 10.

17 Claims, 12 Drawing Sheets

Figure 3A:
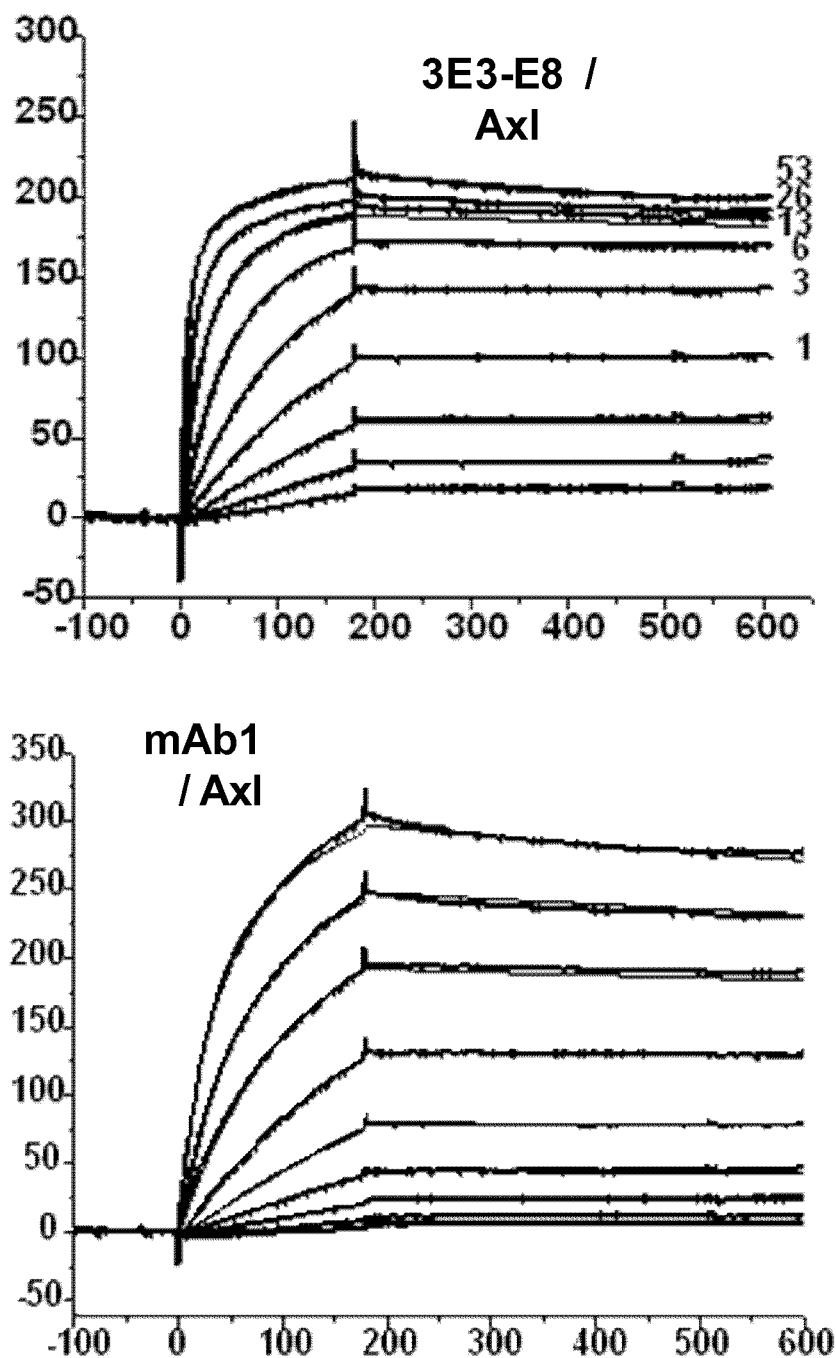

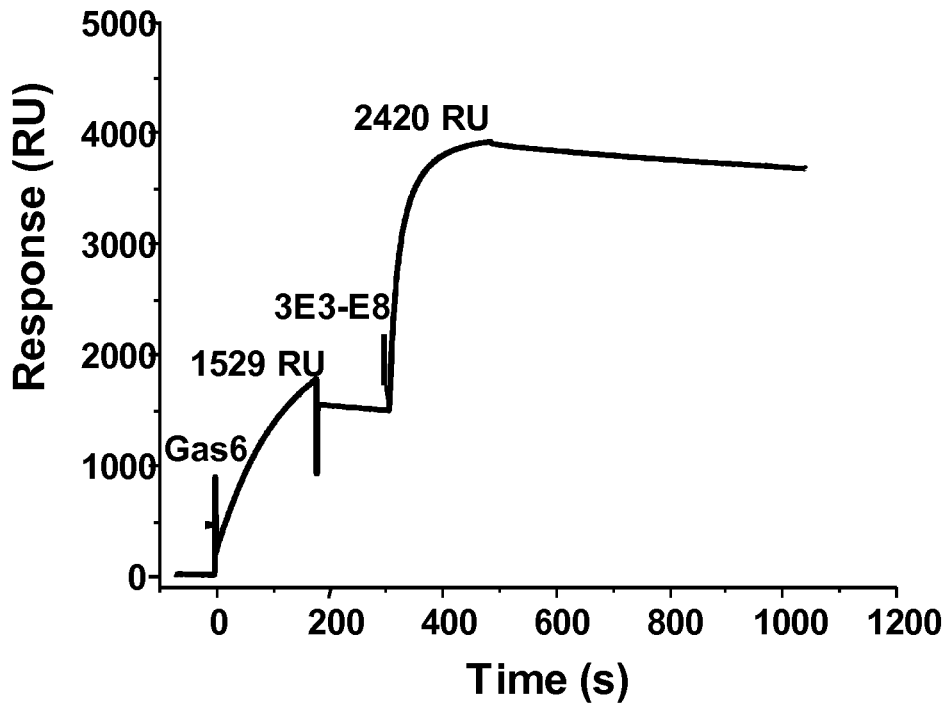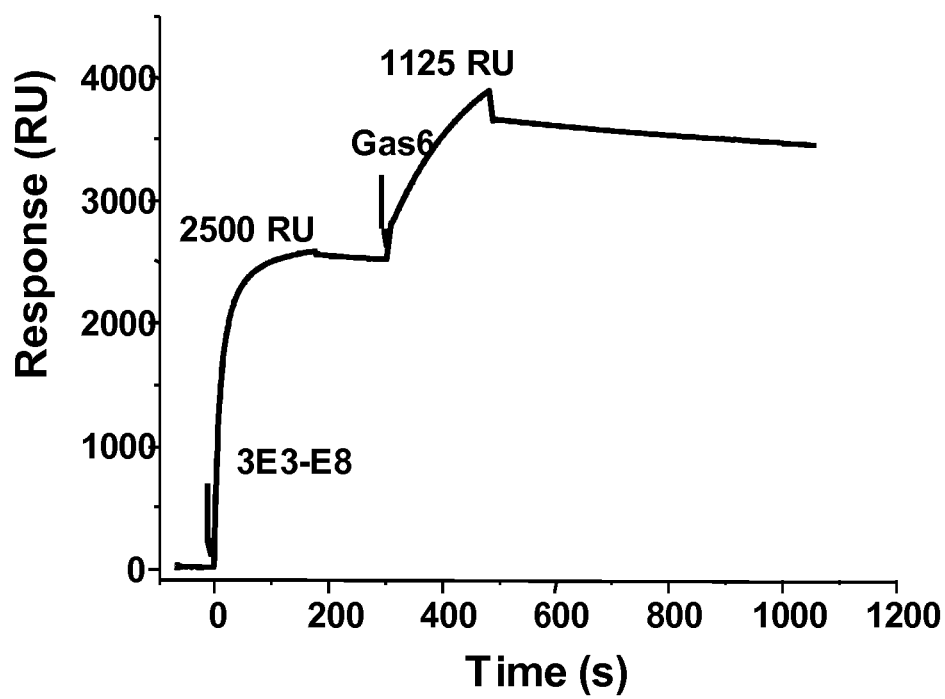
Figure 3B hAxl-hFc composition

| Human Axl (Glu33-Pro440) | DIEGRMD | Human IgG1 (Pro100-Lys330) | 6His tag |

33
EESPFVGN PGNITGARGL TGTLRCQLQV QGEPPEVHWL RDGQIILELAD STQTQVPLGE DEQDDWIVVS QLRITSLQLS
DIGQYQCLVF LGHQTFVSQP GYVGLEGLPY FLEEPEDRTV AANTPFNLSC QAAGPPEPVD LLWLQDAVPL ATAPGHGPQR
SLHVPGLNKT SSFSCEAHNA KGVTTSRTAT ITVLPQQPRN LHLVSRQPTE LEVAWTPGLS GIYPLTHCTL QAVLSNDGMG
IQAGEPDPPE EPLTSQASVP PHQLRLGSLH PHTPYHIRVA CTSSQGPSSW THWLPVETPE GVPLGPPENI SATRNGSQAF
VHWQEPRAPL QGTLLGYRLA YQGQDTPEVL MDIGLRQEVT LELQGDGSVS NLTVCVAAYT AAGDGPWSLP VPLEAWRPVK
440
EPSTPAFSWP DIEGRMDPKS CDKTHTCPPC PAPELLGGPS VFLFPPKPKD TLMISRTPEV TCVVVDVSHE DPEVKFNWYV
DGVEVHNAKT KPREEQYNST YRVVSVLTVL HQDWLNGKEY KCKVSNKALP APIEKTISKA KGQPREPQVY TLPPSRDELT
KNQVSLTCLV KGFYPSDIAV EWESNGQPEN NYKTTPPVLD SDGSFFLYSK LTVDKSRWQQ GNVFSCSVMH EALHNHYTQK
SLSLSPGKHH HHHH

| 3E3-E8 epitope | NLHLVSR (FNIII-1: 230-236) |
| | VLMDIGLRQEVTLE (FNIII-2: 379-392) |

IgG like domain 1
IgG like domain 2
FNIII domain 1
FNIII domain 2

Figure 9

US 9,409,988 B2

ANTI-AXL ANTIBODIES AND USES THEREOF

The present application is filed pursuant to 35 U.S.C. 371 as a U.S. National Phase application of International Patent Application No. PCT/EP2012/062115, which was filed Jun. 22, 2012, claiming the benefit of priority to European Patent Application No. 11305792.1, which was filed on Jun. 22, 2011, and U.S. Provisional Patent Application No. 61/504,256. The entire text of the aforementioned applications is incorporated herein by reference in its entirety.

FIELD OF THE INVENTION

The present invention relates to anti-Axl antibodies and uses thereof in diagnostic and therapeutic methods.

BACKGROUND OF THE INVENTION

Axl belongs to the TAM subfamily of receptor tyrosine kinases (RTKs) that also includes Tyro3 and Mer. The TAM receptors are characterized by a combination of two immunoglobin-like domains and dual fibronectin type III repeats in the extracellular region and a cytoplasmic kinase domain. The ligands for TAM receptors are Gas6 (growth-arrest-specific 6) and protein S, two vitamin-K dependent proteins that show 43% amino acid sequence identity and share similar domain structures. Each protein has an N-terminal Gla domain containing 11 g-carboxyglutamic acid residues, followed by four epidermal growth factor (EGF)-like modules, and a C-terminal sex hormone-binding globlin (SHBG)-like structure consisting of two tandem laminin G domains. The SHBG domain is both necessary and sufficient for TAM receptor binding and activation, whereas the Gla domain binds the negatively charged membrane phospholipids and plays an important role in TAM-mediated phagocytosis of apoptotic cells. TAM activation and signalling has been implicated in multiple cellular responses including cell survival, proliferation, migration and adhesion.

Dysregulation of Axl or its ligand Gas6 is implicated in the pathogenesis of a variety of human cancers. Overexpression of Axl has been reported in a wide array of human cancers (lung, prostate, breast, gastric, pancreatic, ovarian, thyroid, blood cancers, renal cell carcinoma as well as glioblastoma . . . ) and is associated with invasiveness, metastasis and negative prognosis. These findings suggest that Axl may be involved in the regulation of multiple aspects of tumorigenesis including tumor growth, invasion and angiogenesis and thus represents a target for therapeutic intervention in cancer especially for the development of anti-metastatic cancer therapy and for other multiple cancer treatment including treatment of drug resistance.

Accordingly, anti-Axl monoclonal antibodies have been described for use in the treatment of cancers. For example publications relating to anti-Axl antibodies include WO2009/063965, WO2009/062690, and WO2011/014457.

Other roles of Axl dependent or not of its ligands such as inhibition of immune functions, activation of platelet aggregation and viral infection inducer (as an example, Ebola and Lassa virus uptake is promoted by Axl) highlight the potential of Axl as therapeutic target for other applications than oncology.

SUMMARY OF THE INVENTION

The present invention relates to a monoclonal antibody having specificity for Axl, comprising an heavy chain variable region comprising SEQ ID NO:2 in the H-CDR1 region, SEQ ID NO:3 in the H-CDR2 region and SEQ ID NO:4 in the H-CDR3 region; and a light chain variable region comprising SEQ ID NO:6 in the L-CDR1 region, SEQ ID NO:7 in the L-CDR2 region and SEQ ID NO:8 in the L-CDR3 region. Said monoclonal antibody binds to the extracellular domain of Axl via, SEQ ID NO:9 and SEQ ID NO:10.

DETAILED DESCRIPTION OF THE INVENTION

Definitions

The term "Axl" has its general meaning in the art and refers to the human Axl. Axl is also known as "Ark", "Tyro-7", "ufo", or "jtk11".

The term "anti-Axl antibody" refers to an antibody directed against Axl.

According to the present invention, "antibody" or "immunoglobulin" have the same meaning, and will be used equally in the present invention. The term "antibody" as used herein refers to immunoglobulin molecules and immunologically active portions of immunoglobulin molecules, i.e., molecules that contain an antigen binding site that immunospecifically binds an antigen. As such, the term antibody encompasses not only whole antibody molecules, but also antibody fragments as well as variants (including derivatives) of antibodies and antibody fragments. In natural antibodies, two heavy chains are linked to each other by disulfide bonds and each heavy chain is linked to a light chain by a disulfide bond. There are two types of light chain, lambda (l) and kappa (k). There are five main heavy chain classes (or isotypes) which determine the functional activity of an antibody molecule: IgM, IgD, IgG, IgA and IgE. Each chain contains distinct sequence domains. The light chain includes two domains, a variable domain (VL) and a constant domain (CL). The heavy chain includes four domains, a variable domain (VH) and three constant domains (CH1, CH2 and CH3, collectively referred to as CH). The variable regions of both light (VL) and heavy (VH) chains determine binding recognition and specificity to the antigen. The constant region domains of the light (CL) and heavy (CH) chains confer important biological properties such as antibody chain association, secretion, trans-placental mobility, complement binding, and binding to Fc receptors (FcR). The Fv fragment is the N-terminal part of the Fab fragment of an immunoglobulin and consists of the variable portions of one light chain and one heavy chain. The specificity of the antibody resides in the structural complementarity between the antibody combining site and the antigenic determinant. Antibody combining sites are made up of residues that are primarily from the hypervariable or complementarity determining regions (CDRs). Occasionally, residues from nonhypervariable or framework regions (FR) influence the overall domain structure and hence the combining site. Complementarity Determining Regions or CDRs refer to amino acid sequences which together define the binding affinity and specificity of the natural Fv region of a native immunoglobulin binding site. The light and heavy chains of an immunoglobulin each have three CDRs, designated L-CDR1, L-CDR2, L-CDR3 and H-CDR1, H-CDR2, H-CDR3, respectively. An antigen-binding site, therefore, includes six CDRs, comprising the CDR set from each of a heavy and a light chain V region. Framework Regions (FRs) refer to amino acid sequences interposed between CDRs.

The term "chimeric antibody" refers to an antibody which comprises a VH domain and a VL domain of an antibody derived the 3E3E8 antibody, and a CH domain and a CL domain of a human antibody.

According to the invention, the term "humanized antibody" refers to an antibody having variable region framework and constant regions from a human antibody but retains the CDRs of the 3E3E8 antibody.

The term "Fab" denotes an antibody fragment having a molecular weight of about 50,000 and antigen binding activity, in which about a half of the N-terminal side of H chain and the entire L chain, among fragments obtained by treating IgG with a protease, papaine, are bound together through a disulfide bond.

The term "F(ab')2" refers to an antibody fragment having a molecular weight of about 100,000 and antigen binding activity, which is slightly larger than the Fab bound via a disulfide bond of the hinge region, among fragments obtained by treating IgG with a protease, pepsin.

The term "Fab'" refers to an antibody fragment having a molecular weight of about 50,000 and antigen binding activity, which is obtained by cutting a disulfide bond of the hinge region of the F(ab')2.

A single chain Fv ("scFv") polypeptide is a covalently linked VH::VL heterodimer which is usually expressed from a gene fusion including VH and VL encoding genes linked by a peptide-encoding linker. "dsFv" is a VH::VL heterodimer stabilised by a disulfide bond. Divalent and multivalent antibody fragments can form either spontaneously by association of monovalent scFvs, or can be generated by coupling monovalent scFvs by a peptide linker, such as divalent sc(Fv)2.

The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites.

By "purified" and "isolated" it is meant, when referring to an antibody according to the invention or to a nucleotide sequence, that the indicated molecule is present in the substantial absence of other biological macromolecules of the same type. The term "purified" as used herein preferably means at least 75% by weight, more preferably at least 85% by weight, more preferably still at least 95% by weight, and most preferably at least 98% by weight, of biological macromolecules of the same type are present. An "isolated" nucleic acid molecule which encodes a particular polypeptide refers to a nucleic acid molecule which is substantially free of other nucleic acid molecules that do not encode the polypeptide; however, the molecule may include some additional bases or moieties which do not deleteriously affect the basic characteristics of the composition.

Antibodies of the Invention:

The present invention provides for isolated anti-Axl antibodies or fragments thereof. In particular, the inventors have raised a murine anti-Axl antibody (3E3E8) producing hybridoma. The inventors have cloned and characterized the variable domain of the light and heavy chains of said mAb 3E3E8, and thus determined the complementary determining regions (CDRs) domain of said antibody as described in Table 1:

| mAb 3E3E8 Domains | Sequence |
| --- | --- |
| VH | QVQLKESGPGLVAPSQSLSITCSVSGFSLTNYAVHWVRQPP GKGLEWLGVIWAGGSTNYNSALMSRLRISKDNSKSQVFFKM NSLQTDDTAMYYCARYYGSSLYPMDYWGQGTSVTVSS (SEQ ID NO: 1) |
| H-CDR1 | NYAVH (SEQ ID NO: 2) |
| H-CDR2 | VIWAGGSTNYNSALMS (SEQ ID NO: 3) |
| H-CDR3 | YYGSSLYPMDY (SEQ ID NO: 4) |
| VL | DIVMTQAAPSVPVTPGESVSISCRSSKSLLHSNGNTYLYWF LQRPGQSPQLLIYRMSNLASGVPDRFSGSGSGTVFTLRISG VEAEDVGVYYCMQHLEYPWTFGGGTELEIK (SEQ ID NO: 5) |
| L-CDR1 | RSSKSLLHSNGNTYLY (SEQ ID NO: 6) |
| L-CDR2 | RMSNLA (SEQ ID NO: 7) |
| L-CDR3 | MQHLEYPWT (SEQ ID NO: 8) |

Therefore, the invention relates to a monoclonal antibody having specificity for Axl, comprising a heavy chain wherein the variable domain comprises at least one CDR having a sequence selected from the group consisting of SEQ ID NO:2 for H-CDR1, SEQ ID NO:3 for H-CDR2 and SEQ ID NO:4 for H-CDR3.

The invention also relates to a monoclonal antibody having specificity for Axl, comprising a light chain wherein the variable domain comprises at least one CDR having a sequence selected from the group consisting of SEQ ID NO:6 for L-CDR1, SEQ ID NO:7 for L-CDR2 and SEQ ID NO:8 for L-CDR3.

The monoclonal antibody of the invention, may comprise a heavy chain wherein the variable domain comprises at least one CDR having a sequence selected from the group consisting of SEQ ID NO:2 for H-CDR1, SEQ ID NO:3 for H-CDR2 and SEQ ID NO:4 for H-CDR3 and a light chain wherein the variable domain comprises at least one CDR having a sequence selected from the group consisting of SEQ ID NO:6 for L-CDR1, SEQ ID NO:7 for L-CDR2 and SEQ ID NO:8 for L-CDR3.

In particular, the invention provides an anti-Axl monoclonal antibody comprising:
an heavy chain variable region comprising SEQ ID NO:2 in the H-CDR1 region, SEQ ID NO:3 in the H-CDR2 region and SEQ ID NO:4 in the H-CDR3 region; and
a light chain variable region comprising SEQ ID NO:6 in the L-CDR1 region, SEQ ID NO:7 in the L-CDR2 region and SEQ ID NO:8 in the L-CDR3 region.

In a particular embodiment, the heavy chain variable region of said antibody has the amino acid sequence set forth as SEQ ID NO: 1 and/or the light chain variable region has the amino acid sequence set forth as SEQ ID NO: 5.

In another embodiment, the monoclonal antibody of the invention is a chimeric antibody, preferably a chimeric mouse/human antibody. In particular, said mouse/human chimeric antibody may comprise the variable domains of 3E3E8 antibody as defined above.

In another embodiment, the monoclonal of the invention is a humanized antibody. In particular, in said humanized antibody, the variable domain comprises human acceptor frameworks regions, and optionally human constant domain where present, and non-human donor CDRs, such as mouse CDRs as defined above.

The invention further provides anti-Axl fragments directed against Axl of said antibodies which include but are not limited to Fv, Fab, F(ab')2, Fab', dsFv, scFv, sc(Fv)2 and diabodies.

The invention further provides anti-Axl antibody or fragments that bind to amino acid sequences SEQ ID NO:9 and SEQ ID NO:10 in the extracellular part of Axl.

| mAb 3E3E8 | Human Axl sequence (epitope) |
|---|---|
| FN3 domain 1 | NLHLVSR (SEQ ID NO: 9) |
| FN3 domain 2 | VLMDIGLRQEVTLE (SEQ ID NO: 10) |

In another aspect, the invention relates to a polypeptide which has a sequence selected from the group consisting of SEQ ID NO: 1, SEQ ID NO:2, SEQ ID NO:3, SEQ ID NO:4, SEQ ID NO:5; SEQ ID NO: 6; SEQ ID NO:7 and SEQ ID NO:8.

Methods of Producing Antibodies of the Invention:

Anti-Axl antibodies of the invention may be produced by any technique known in the art, such as, without limitation, any chemical, biological, genetic or enzymatic technique, either alone or in combination.

Knowing the amino acid sequence of the desired sequence, one skilled in the art can readily produce said antibodies, by standard techniques for production of polypeptides. For instance, they can be synthesized using well-known solid phase method, preferably using a commercially available peptide synthesis apparatus (such as that made by Applied Biosystems, Foster City, Calif.) and following the manufacturer's instructions. Alternatively, antibodies of the invention can be synthesized by recombinant DNA techniques well-known in the art. For example, antibodies can be obtained as DNA expression products after incorporation of DNA sequences encoding the antibodies into expression vectors and introduction of such vectors into suitable eukaryotic or prokaryotic hosts that will express the desired antibodies, from which they can be later isolated using well-known techniques.

Accordingly, a further object of the invention relates to a nucleic acid sequence encoding an antibody according to the invention. More particularly the nucleic acid sequence encodes an heavy chain or a light chain of an antibody of the invention.

Typically, said nucleic acid is a DNA or RNA molecule, which may be included in any suitable vector, such as a plasmid, cosmid, episome, artificial chromosome, phage or a viral vector.

The terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence.

So, a further object of the invention relates to a vector comprising a nucleic acid of the invention.

Such vectors may comprise regulatory elements, such as a promoter, enhancer, terminator and the like, to cause or direct expression of said antibody upon administration to a subject. Examples of promoters and enhancers used in the expression vector for animal cell include early promoter and enhancer of SV40 (Mizukami T. et al. 1987), LTR promoter and enhancer of Moloney mouse leukemia virus (Kuwana Y et al. 1987), promoter (Mason J O et al. 1985) and enhancer (Gillies S D et al. 1983) of immunoglobulin H chain and the like.

Any expression vector for animal cell can be used, so long as a gene encoding the human antibody C region can be inserted and expressed. Examples of suitable vectors include pAGE107 (Miyaji H et al. 1990), pAGE103 (Mizukami T et al. 1987), pHSG274 (Brady G et al. 1984), pKCR(O'Hare K et al. 1981), pSG1 beta d2-4-(Miyaji H et al. 1990) and the like.

Other examples of plasmids include replicating plasmids comprising an origin of replication, or integrative plasmids, such as for instance pUC, pcDNA, pBR, and the like.

Other examples of viral vector include adenoviral, retroviral, herpes virus and AAV vectors. Such recombinant viruses may be produced by techniques known in the art, such as by transfecting packaging cells or by transient transfection with helper plasmids or viruses. Typical examples of virus packaging cells include PA317 cells, PsiCRIP cells, GPenv+ cells, 293 cells, etc. Detailed protocols for producing such replication-defective recombinant viruses may be found for instance in WO 95/14785, WO 96/22378, U.S. Pat. Nos. 5,882,877, 6,013,516, 4,861,719, 5,278,056 and WO 94/19478.

A further object of the present invention relates to a host cell which has been transfected, infected or transformed by a nucleic acid and/or a vector according to the invention.

The term "transformation" means the introduction of a "foreign" (i.e. extrinsic or extracellular) gene, DNA or RNA sequence to a host cell, so that the host cell will express the introduced gene or sequence to produce a desired substance, typically a protein or enzyme coded by the introduced gene or sequence. A host cell that receives and expresses introduced DNA or RNA bas been "transformed".

The nucleic acids of the invention may be used to produce an antibody of the invention in a suitable expression system. The term "expression system" means a host cell and compatible vector under suitable conditions, e.g. for the expression of a protein coded for by foreign DNA carried by the vector and introduced to the host cell.

Common expression systems include E. coli host cells and plasmid vectors, insect host cells and Baculovirus vectors, and mammalian host cells and vectors. Other examples of host cells include, without limitation, prokaryotic cells (such as bacteria) and eukaryotic cells (such as yeast cells, mammalian cells, insect cells, plant cells, etc.). Specific examples include E. coli, Kluyveromyces or Saccharomyces yeasts, mammalian cell lines (e.g., Vero cells, CHO cells, 3T3 cells, COS cells, etc.) as well as primary or established mammalian cell cultures (e.g., produced from lymphoblasts, fibroblasts, embryonic cells, epithelial cells, nervous cells, adipocytes, etc.). Examples also include mouse SP2/0-Ag14 cell (ATCC CRL1581), mouse P3X63-Ag8.653 cell (ATCC CRL1580), CHO cell in which a dihydrofolate reductase gene (hereinafter referred to as "DHFR gene") is defective (Urlaub G et al; 1980), rat YB2/3HL.P2.G11.16Ag.20 cell (ATCC CRL1662, hereinafter referred to as "YB2/0 cell"), and the like.

The present invention also relates to a method of producing a recombinant host cell expressing an antibody according to the invention, said method comprising the steps of: (i) introducing in vitro or ex vivo a recombinant nucleic acid or a vector as described above into a competent host cell, (ii) culturing in vitro or ex vivo the recombinant host cell obtained and (iii), optionally, selecting the cells which express and/or secrete said antibody. Such recombinant host cells can be used for the production of antibodies of the invention.

In another particular embodiment, the method comprises the steps of:

(i) culturing the hybridoma 3E3E8 under conditions suitable to allow expression of 3E3E8 antibody; and (ii) recovering the expressed antibody.

Antibodies of the invention are suitably separated from the culture medium by conventional immunoglobulin purification procedures such as, for example, protein A-Sepharose, hydroxylapatite chromatography, gel electrophoresis, dialysis, or affinity chromatography.

In a particular embodiment, the human chimeric antibody of the present invention can be produced by obtaining nucleic sequences encoding VL and VH domains as previously described, constructing a human chimeric antibody expression vector by inserting them into an expression vector for animal cell having genes encoding human antibody CH and human antibody CL, and expressing the coding sequence by introducing the expression vector into an animal cell.

As the CH domain of a human chimeric antibody, it may be any region which belongs to human immunoglobulin, but those of IgG class are suitable and any one of subclasses belonging to IgG class, such as IgG1, IgG2, IgG3 and IgG4, can also be used. Also, as the CL of a human chimeric antibody, it may be any region which belongs to Ig, and those of kappa class or lambda class can be used.

Methods for producing chimeric antibodies involve conventional recombinant DNA and gene transfection techniques are well known in the art (See Morrison S L. et al. (1984) and patent documents U.S. Pat. Nos. 5,202,238; and 5,204,244).

The humanized antibody of the present invention may be produced by obtaining nucleic acid sequences encoding CDR domains, as previously described, constructing a humanized antibody expression vector by inserting them into an expression vector for animal cell having genes encoding (i) a heavy chain constant region identical to that of a human antibody and (ii) a light chain constant region identical to that of a human antibody, and expressing the genes by introducing the expression vector into an animal cell.

The humanized antibody expression vector may be either of a type in which a gene encoding an antibody heavy chain and a gene encoding an antibody light chain exists on separate vectors or of a type in which both genes exist on the same vector (tandem type). In respect of easiness of construction of a humanized antibody expression vector, easiness of introduction into animal cells, and balance between the expression levels of antibody H and L chains in animal cells, humanized antibody expression vector of the tandem type is preferred (Shitara K et al. 1994). Examples of tandem type humanized antibody expression vector include pKANTEX93 (WO 97/10354), pEE18 and the like.

Methods for producing humanized antibodies based on conventional recombinant DNA and gene transfection techniques are well known in the art (See, e.g., Riechmann L. et al. 1988; Neuberger M S. et al. 1985). Antibodies can be humanized using a variety of techniques known in the art including, for example, CDR-grafting (EP 239,400; PCT publication WO91/09967; U.S. Pat. Nos. 5,225,539; 5,530,101; and 5,585,089), veneering or resurfacing (EP 592,106; EP 519, 596; Padlan E A (1991); Studnicka G M et al. (1994); Roguska M A. et al. (1994)), and chain shuffling (U.S. Pat. No. 5,565,332). The general recombinant DNA technology for preparation of such antibodies is also known (see European Patent Application EP 125023 and International Patent Application WO 96/02576).

The Fab of the present invention can be obtained by treating an antibody which specifically reacts with Axl with a protease, papaine. Also, the Fab can be produced by inserting DNA encoding Fab of the antibody into a vector for prokaryotic expression system, or for eukaryotic expression system, and introducing the vector into a procaryote or eucaryote (as appropriate) to express the Fab.

The F(ab')2 of the present invention can be obtained treating an antibody which specifically reacts with Axl with a protease, pepsin. Also, the F(ab')2 can be produced by binding Fab' described below via a thioether bond or a disulfide bond.

The Fab' of the present invention can be obtained treating F(ab')2 which specifically reacts with Axl with a reducing agent, dithiothreitol. Also, the Fab' can be produced by inserting DNA encoding Fab' fragment of the antibody into an expression vector for prokaryote, or an expression vector for eukaryote, and introducing the vector into a prokaryote or eukaryote (as appropriate) to perform its expression.

The scFv of the present invention can be produced by obtaining cDNA encoding the VH and VL domains as previously described, constructing DNA encoding scFv, inserting the DNA into an expression vector for prokaryote, or an expression vector for eukaryote, and then introducing the expression vector into a prokaryote or eukaryote (as appropriate) to express the scFv. To generate a humanized scFv fragment, a well known technology called CDR grafting may be used, which involves selecting the complementary determining regions (CDRs) from a donor scFv fragment, and grafting them onto a human scFv fragment framework of known three dimensional structure (see, e.g., WO98/45322; WO 87/02671; U.S. Pat. Nos. 5,859,205; 5,585,089; 4,816, 567; EP0173494).

Amino acid sequence modification(s) of the antibodies described herein are contemplated. For example, it may be desirable to improve the binding affinity and/or other biological properties of the antibody. It is known that when a humanized antibody is produced by simply grafting only CDRs in VH and VL of an antibody derived from a non-human animal in FRs of the VH and VL of a human antibody, the antigen binding activity is reduced in comparison with that of the original antibody derived from a non-human animal. It is considered that several amino acid residues of the VH and VL of the non-human antibody, not only in CDRs but also in FRs, are directly or indirectly associated with the antigen binding activity. Hence, substitution of these amino acid residues with different amino acid residues derived from FRs of the VH and VL of the human antibody would reduce of the binding activity. In order to resolve the problem, in antibodies grafted with human CDR, attempts have to be made to identify, among amino acid sequences of the FR of the VH and VL of human antibodies, an amino acid residue which is directly associated with binding to the antibody, or which interacts with an amino acid residue of CDR, or which maintains the three-dimensional structure of the antibody and which is directly associated with binding to the antigen. The reduced antigen binding activity could be increased by replacing the identified amino acids with amino acid residues of the original antibody derived from a non-human animal.

Modifications and changes may be made in the structure of the antibodies of the present invention, and in the DNA sequences encoding them, and still obtain a functional molecule that encodes an antibody with desirable characteristics.

In making the changes in the amino sequences, the hydropathic index of amino acids may be considered. The importance of the hydropathic amino acid index in conferring interactive biologic function on a protein is generally understood in the art. It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of their hydrophobicity and charge characteristics these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophane (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

A further object of the present invention also encompasses function-conservative variants of the antibodies of the present invention.

"Function-conservative variants" are those in which a given amino acid residue in a protein or enzyme has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like). Amino acids other than those indicated as conserved may differ in a protein so that the percent protein or amino acid sequence similarity between any two proteins of similar function may vary and may be, for example, from 70% to 99% as determined according to an alignment scheme such as by the Cluster Method, wherein similarity is based on the MEGA-LIGN algorithm. A "function-conservative variant" also includes a polypeptide which has at least 60% amino acid identity as determined by BLAST or FASTA algorithms, preferably at least 75%, more preferably at least 85%, still preferably at least 90%, and even more preferably at least 95%, and which has the same or substantially similar properties or functions as the native or parent protein to which it is compared.

Two amino acid sequences are "substantially homologous" or "substantially similar" when greater than 80%, preferably greater than 85%, preferably greater than 90% of the amino acids are identical, or greater than about 90%, preferably greater than 95%, are similar (functionally identical) over the whole length of the shorter sequence. Preferably, the similar or homologous sequences are identified by alignment using, for example, the GCG (Genetics Computer Group, Program Manual for the GCG Package, Version 7, Madison, Wis.) pileup program, or any of sequence comparison algorithms such as BLAST, FASTA, etc.

For example, certain amino acids may be substituted by other amino acids in a protein structure without appreciable loss of activity. Since the interactive capacity and nature of a protein define the protein's biological functional activity, certain amino acid substitutions can be made in a protein sequence, and, of course, in its DNA encoding sequence, while nevertheless obtaining a protein with like properties. It is thus contemplated that various changes may be made in the antibodies sequences of the invention, or corresponding DNA sequences which encode said antibodies, without appreciable loss of their biological activity.

It is known in the art that certain amino acids may be substituted by other amino acids having a similar hydropathic index or score and still result in a protein with similar biological activity, i.e. still obtain a biological functionally equivalent protein.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

Accordingly, the invention also provides an antibody comprising a heavy chain wherein the variable domain comprises:

a H-CDR1 having at least 90% or 95% identity with sequence set forth as SEQ ID NO: 2,
a H-CDR2 having at least 90% or 95% identity with sequence set forth as SEQ ID NO: 3,
a H-CDR3 having at least 90% or 95% identity with sequence set forth as SEQ ID NO: 4,
a L-CDR1 having at least 90% or 95% identity with sequence set forth as SEQ ID NO: 6,
a L-CDR2 having at least 90% or 95% identity with sequence set forth as SEQ ID NO: 7,
a L-CDR3 having at least 90% or 95% identity with sequence set forth as SEQ ID NO: 8, and
that specifically binds to Axl with substantially the same affinity as an antibody comprising a heavy chain wherein the variable domain comprises SEQ ID NO: 2 for H-CDR1, SEQ ID NO: 3 for H-CDR2 and SEQ ID NO: 4 for H-CDR3 and a light chain wherein the variable domain comprises SEQ ID NO: 6 for L-CDR1, SEQ ID NO: 7 for L-CDR2 and SEQ ID NO: 8 for L-CDR3, and more preferably with substantially the same affinity as the murine anti-Axl antibody 3E3E8.

Accordingly, the invention also provides an antibody which binds to FN3 domain 1 and FN3 domain 2 of the extracellular part of Axl (epitope amino acid sequences of Axl SEQ ID NO:9 and SEQ ID:10).

Said antibodies may be assayed for specific binding by any method known in the art. Many different competitive binding assay format(s) can be used for epitope binning. The immunoassays which can be used include, but are not limited to, competitive assay systems using techniques such western blots, radioimmunoassays, ELISA, "sandwich" immunoassays, immunoprecipitation assays, precipitin assays, gel diffusion precipitin assays, immunoradiometric assays, fluorescent immunoassays, protein A immunoassays, and complement-fixation assays. Such assays are routine and well known in the art (see, e.g., Ausubel et al., eds, 1994 Current Protocols in Molecular Biology, Vol. 1, John Wiley & sons, Inc., New York). For example, the BIACORE® (GE Healthcare, Piscataway, N.J.) is one of a variety of surface plasmon resonance assay formats that are routinely used to epitope bin panels of monoclonal antibodies. Additionally, routine cross-blocking assays such as those described in Antibodies, A Laboratory Manual, Cold Spring Harbor Laboratory, Ed Harlow and David Lane, 1988, can be performed.

Engineered antibodies of the invention include those in which modifications have been made to framework residues within VH and/or VL, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "backmutated" to the germline sequence by, for example, site-directed mutagenesis or PCR-mediated mutagenesis. Such "backmutated" antibodies are also intended to be encompassed by the invention. Another type of framework modification involves mutating one or more residues within the framework region, or even within one or more CDR regions, to remove T cell-epitopes to thereby reduce the potential immunogenicity of the antibody. This approach is also referred to as "deimmunization" and is described in further detail in U.S. Patent Publication No. 20030153043 by Carr et al.

In addition or alternative to modifications made within the framework or CDR regions, antibodies of the invention may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the invention may be chemically modified (e.g., one or more chemical moieties can be attached to the antibody) or be modified to alter its glycosylation, again to alter one or more functional properties of the antibody. Each of these embodiments is described in further detail below. The numbering of residues in the Fc region is that of the EU index of Kabat.

In one embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In another embodiment, the Fc hinge region of an antibody is mutated to decrease the biological half-life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In another embodiment, the antibody is modified to increase its biological half-life. Various approaches are possible. For example, one or more of the following mutations can be introduced: T252L, T254S, T256F, as described in U.S. Pat. No. 6,277,375 by Ward. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

In yet other embodiments, the Fc region is altered by replacing at least one amino acid residue with a different amino acid residue to alter the effector functions of the antibody. For example, one or more amino acids can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al.

In another embodiment, one or more amino acids selected from amino acid residues can be replaced with a different amino acid residue such that the antibody has altered C1q binding and/or reduced or abolished complement dependent cytotoxicity (CDC). This approach is described in further detail in U.S. Pat. No. 6,194,551 by ldusogie et al.

In another embodiment, one or more amino acid residues are altered to thereby alter the ability of the antibody to fix complement. This approach is described further in PCT Publication WO 94/29351 by Bodmer et al.

In yet another embodiment, the Fc region is modified to increase the ability of the antibody to mediate antibody dependent cellular cytotoxicity (ADCC) and/or to increase the affinity of the antibody for an Fc receptor by modifying one or more amino acids. This approach is described further in PCT Publication WO 00/42072 by Presta. Moreover, the binding sites on human IgGI for FcγRI, FcγRII, FcγRIII and FcRn have been mapped and variants with improved binding have been described (see Shields, R. L. et al., 2001 J. Biol. Chen. 276:6591-6604, WO2010106180).

In still another embodiment, the glycosylation of an antibody is modified. For example, an aglycoslated antibody can be made (i.e., the antibody lacks glycosylation). Glycosylation can be altered to, for example, increase the affinity of the antibody for the antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al.

Additionally or alternatively, an antibody can be made that has an altered type of glycosylation, such as a hypofucosylated or non-fucosylated antibody having reduced amounts of or no fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. For example, EP 1,176,195 by Hang et al. describes a cell line with a functionally disrupted FUT8 gene, which encodes a fucosyl transferase, such that antibodies expressed in such a cell line exhibit hypofucosylation or are devoid of fucosyl residues. Therefore, in one embodiment, the antibodies of the invention may be produced by recombinant expression in a cell line which exhibit hypofucosylation or non-fucosylation pattern, for example, a mammalian cell line with deficient expression of the FUT8 gene encoding fucosyltransferase. PCT Publication WO 03/035835 by Presta describes a variant CHO cell line, Lecl3 cells, with reduced ability to attach fucose to Asn(297)-linked carbohydrates, also resulting in hypofucosylation of antibodies expressed in that host cell (see also Shields, R. L. et al., 2002 J. Biol. Chem, 277:26733-26740). PCT Publication WO 99/54342 by Umana et al. describes cell lines engineered to express glycoprotein-modifying glycosyl transferases (e.g., beta(1,4)—N acetylglucosaminyltransferase lll (GnTlll)) such that antibodies expressed in the engineered cell lines exhibit increased bisecting GlcNac structures which results in increased ADCC activity of the antibodies (see also Umana et al., 1999 Nat. Biotech. 17:176-180). Eureka Therapeutics further describes genetically engineered CHO mammalian cells capable of producing antibodies with altered mammalian glycosylation pattern devoid of fucosyl residues www.eurekainc.com/a&boutuscompanyoverview.html), Alternatively, the antibodies of the invention can be produced in yeasts or filamentous fungi engineered for mammalian-like glycosylation pattern and capable of producing antibodies lacking fucose as glycosylation pattern (see for example EP1297172B1).

Another modification of the antibodies herein that is contemplated by the invention is pegylation. An antibody can be pegylated to, for example, increase the biological (e.g., serum) half-life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. The pegylation can be carried out by an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the invention. See for example, EP O 154 316 by Nishimura et al. and EP 0 401 384 by Ishikawa et al.

Another modification of the antibodies that is contemplated by the invention is a conjugate or a protein fusion of at least the antigen-binding region of the antibody of the invention to serum protein, such as human serum albumin or a fragment thereof to increase half-life of the resulting molecule. Such approach is for example described in Ballance et al. EP0322094.

Another possibility is a fusion of at least the antigen-binding region of the antibody of the invention to proteins capable of binding to serum proteins, such human serum albumin to increase half life of the resulting molecule. Such approach is for example described in Nygren et al., EP 0 486 525.

Immunoconjugates:

An antibody of the invention can be conjugated with a detectable label to form an anti-Axl immunoconjugate. Suitable detectable labels include, for example, a radioisotope, a fluorescent label, a chemiluminescent label, an enzyme label, a bioluminescent label or colloidal gold. Methods of making and detecting such detectably-labeled immunoconjugates are well-known to those of ordinary skill in the art, and are described in more detail below.

The detectable label can be a radioisotope that is detected by autoradiography. Isotopes that are particularly useful for the purpose of the present invention are $^{3}H$, $^{125}I$, $^{131}I$, $^{35}S$ and $^{14}C$.

Anti-Axl immunoconjugates can also be labeled with a fluorescent compound. The presence of a fluorescently-labeled antibody is determined by exposing the immunoconjugate to light of the proper wavelength and detecting the resultant fluorescence. Fluorescent labeling compounds include fluorescein isothiocyanate, rhodamine, phycoerytherin, phycocyanin, allophycocyanin, o-phthaldehyde and fluorescamine.

Alternatively, anti-Axl immunoconjugates can be detectably labeled by coupling an antibody to a chemiluminescent compound. The presence of the chemiluminescent-tagged immunoconjugate is determined by detecting the presence of luminescence that arises during the course of a chemical reaction. Examples of chemiluminescent labeling compounds include luminol, isoluminol, an aromatic acridinium ester, an imidazole, an acridinium salt and an oxalate ester.

Similarly, a bioluminescent compound can be used to label anti-Axl immunoconjugates of the present invention. Bioluminescence is a type of chemiluminescence found in biological systems in which a catalytic protein increases the efficiency of the chemiluminescent reaction. The presence of a bioluminescent protein is determined by detecting the presence of luminescence. Bioluminescent compounds that are useful for labeling include luciferin, luciferase and aequorin.

Alternatively, anti-Axl immunoconjugates can be detectably labeled by linking an anti-Axl monoclonal antibody to an enzyme. When the anti-Axl-enzyme conjugate is incubated in the presence of the appropriate substrate, the enzyme moiety reacts with the substrate to produce a chemical moiety which can be detected, for example, by spectrophotometric, fluorometric or visual means. Examples of enzymes that can be used to detectably label polyspecific immunoconjugates include β-galactosidase, glucose oxidase, peroxidase and alkaline phosphatase.

Those of skill in the art will know of other suitable labels which can be employed in accordance with the present invention. The binding of marker moieties to anti-Axl monoclonal antibodies can be accomplished using standard techniques known to the art. Typical methodology in this regard is described by Kennedy et al., *Clin. Chim. Acta* 70:1, 1976; Schurs et al., *Clin. Chim. Acta* 81:1, 1977; Shih et al., *Intl J. Cancer* 46:1101, 1990; Stein et al., *Cancer Res.* 50:1330, 1990; and Coligan, supra.

Moreover, the convenience and versatility of immunochemical detection can be enhanced by using anti-Axl monoclonal antibodies that have been conjugated with avidin, streptavidin, and biotin. (See, e.g., Wilchek et al. (eds.), "Avidin-Biotin Technology," *Methods In Enzymology* (Vol. 184) (Academic Press 1990); Bayer et al., "Immunochemical Applications of Avidin-Biotin Technology," in *Methods In Molecular Biology* (Vol. 10) 149-162 (Manson, ed., The Humana Press, Inc. 1992).)

Methods for performing immunoassays are well-established. (See, e.g., Cook and Self, "Monoclonal Antibodies in Diagnostic Immunoassays," in *Monoclonal Antibodies: Production, Engineering, and Clinical Application* 180-208 (Ritter and Ladyman, eds., Cambridge University Press 1995); Perry, "The Role of Monoclonal Antibodies in the Advancement of Immunoassay Technology," in *Monoclonal Antibodies: Principles and Applications* 107-120 (Birch and Lennox, eds., Wiley-Liss, Inc. 1995); Diamandis, Immunoassay (Academic Press, Inc. 1996).)

In another aspect, the present invention provides an anti-Axl monoclonal antibody-drug conjugate. An "anti-Axl monoclonal antibody-drug conjugate" as used herein refers to an anti-Axl monoclonal antibody according to the invention conjugated to a therapeutic agent. Such anti-Axl monoclonal antibody-drug conjugates produce clinically beneficial effects on Axl-expressing cells when administered to a subject, such as, for example, a subject with a Axl-expressing cancer, typically when administered alone but also in combination with other therapeutic agents.

In typical embodiments, an anti-Axl monoclonal antibody is conjugated to a cytotoxic agent, such that the resulting antibody-drug conjugate exerts a cytotoxic or cytostatic effect on a Axl-expressing cell (e.g., a Axl-expressing cancer cell) when taken up or internalized by the cell. Particularly suitable moieties for conjugation to antibodies are chemotherapeutic agents, prodrug converting enzymes, radioactive isotopes or compounds, or toxins. For example, an anti-Axl monoclonal antibody can be conjugated to a cytotoxic agent such as a chemotherapeutic agent or a toxin (e.g., a cytostatic or cytocidal agent such as, for example, abrin, ricin A, pseudomonas exotoxin, or diphtheria toxin).

Useful classes of cytotoxic agents include, for example, antitubulin agents, auristatins, DNA minor groove binders, DNA replication inhibitors, alkylating agents (e.g., platinum complexes such as cis-platin, mono(platinum), bis(platinum) and tri-nuclear platinum complexes and -carboplatin), anthracyclines, antibiotics, antifolates, antimetabolites, chemotherapy sensitizers, duocarmycins, etoposides, fluorinated pyrimidines, ionophores, lexitropsins, nitrosoureas, platinols, pre-forming compounds, purine antimetabolites, puromycins, radiation sensitizers, steroids, taxanes, topoisomerase inhibitors, vinca alkaloids, or the like.

Individual cytotoxic agents include, for example, an androgen, anthramycin (AMC), asparaginase, 5-azacytidine, azathioprine, bleomycin, busulfan, buthionine sulfoximine, camptothecin, carboplatin, carmustine (BSNU), CC-1065 (Li et al., Cancer Res. 42:999-1004, 1982), chlorambucil, cisplatin, colchicine, cyclophosphamide, cytarabine, cytidine arabinoside, cytochalasin B, dacarbazine, dactinomycin (formerly actinomycin), daunorubicin, decarbazine, docetaxel, doxorubicin, an estrogen, 5-fluordeoxyuridine, etopside phosphate (VP-16), 5-fluorouracil, gramicidin D, hydroxyurea, idarubicin, ifosfamide, irinotecan, lomustine (CCNU), mechlorethamine, melphalan, 6-mercaptopurine, methotrexate, mithramycin, mitomycin C, mitoxantrone, nitroimidazole, paclitaxel, plicamycin, procarbizine, streptozotocin, tenoposide (VM-26), 6-thioguanine, thioTEPA, topotecan, vinblastine, vincristine, and vinorelbine.

Particularly suitable cytotoxic agents include, for example, dolastatins (e.g., auristatin E, AFP, MMAF, MMAE), DNA minor groove binders (e.g., enediynes and lexitropsins), duocarmycins, taxanes (e.g., paclitaxel and docetaxel), puromycins, vinca alkaloids, CC-1065, SN-38 (7-ethyl-10-hydroxycamptothein), topotecan, morpholino-doxorubicin, rhizoxin, cyanomorpholino-doxorubicin, echinomycin, combretastatin, netropsin, epothilone A and B, estramustine, cryptophysins, cemadotin, maytansinoids, discodermolide, eleutherobin, and mitoxantrone.

In certain embodiments, a cytotoxic agent is a conventional chemotherapeutic such as, for example, doxorubicin, paclitaxel, melphalan, vinca alkaloids, methotrexate, mitomycin C or etoposide. In addition, potent agents such as CC-1065 analogues, calicheamicin, maytansine, analogues of dolastatin 10, rhizoxin, and palytoxin can be linked to an anti-Axl expressing antibody.

In specific variations, the cytotoxic or cytostatic agent is auristatin E (also known in the art as dolastatin-10) or a derivative thereof. Typically, the auristatin E derivative is, e.g., an ester formed between auristatin E and a keto acid. For example, auristatin E can be reacted with paraacetyl benzoic acid or benzoylvaleric acid to produce AEB and AEVB, respectively. Other typical auristatin derivatives include AFP (dimethylvaline-valine-dolaisoleuine-dolaproine-phenylalanine-p-phenylenediamine), MMAF (dovaline-valine-dolaisoleunine-dolaproine-phenylalanine), and MAE (monomethyl auristatin E). The synthesis and structure of auristatin E and its derivatives are described in U.S. Patent Application Publication No. 20030083263; International Patent Publication Nos. WO 2002/088172 and WO 2004/010957; and U.S. Pat. Nos. 6,884,869; 6,323,315; 6,239,104; 6,034,065; 5,780,588; 5,665,860; 5,663,149; 5,635,483; 5,599,902; 5,554,725; 5,530,097; 5,521,284; 5,504,191; 5,410,024; 5,138,036; 5,076,973; 4,986,988; 4,978,744; 4,879,278; 4,816,444; and 4,486,414.

In other variations, the cytotoxic agent is a DNA minor groove binding agent. (See, e.g., U.S. Pat. No. 6,130,237.) For example, in certain embodiments, the minor groove binding agent is a CBI compound. In other embodiments, the minor groove binding agent is an enediyne (e.g., calicheamicin).

In certain embodiments, an antibody-drug conjugate comprises an anti-tubulin agent. Examples of anti-tubulin agents include, for example, taxanes (e.g., Taxol® (paclitaxel), Taxotere® (docetaxel)), T67 (Tularik), vinca alkyloids (e.g., vincristine, vinblastine, vindesine, and vinorelbine), and dolastatins (e.g., auristatin E, AFP, MMAF, MMAE, AEB, AEVB). Other antitubulin agents include, for example, baccatin derivatives, taxane analogs (e.g., epothilone A and B), nocodazole, colchicine and colcimid, estramustine, cryptophysins, cemadotin, maytansinoids, combretastatins, discodermolide, and eleutherobin. In some embodiments, the cytotoxic agent is a maytansinoid, another group of anti-tubulin agents. For example, in specific embodiments, the maytansinoid is maytansine or DM-1 (ImmunoGen, Inc.; see also Chari et al., Cancer Res. 52:127-131, 1992).

In other embodiments, the cytotoxic agent is an antimetabolite. The antimetabolite can be, for example, a purine antagonist (e.g., azothioprine or mycophenolate mofetil), a dihydrofolate reductase inhibitor (e.g., methotrexate), acyclovir, gangcyclovir, zidovudine, vidarabine, ribavarin, azidothymidine, cytidine arabinoside, amantadine, dideoxyuridine, iododeoxyuridine, poscarnet, or trifluridine.

In other embodiments, an anti-Axl monoclonal antibody is conjugated to a pro-drug converting enzyme. The pro-drug converting enzyme can be recombinantly fused to the antibody or chemically conjugated thereto using known methods. Exemplary pro-drug converting enzymes are carboxypeptidase G2, β-glucuronidase, penicillin-V-amidase, penicillin-G-amidase, β-lactamase, β-glucosidase, nitroreductase and carboxypeptidase A.

Techniques for conjugating therapeutic agents to proteins, and in particular to antibodies, are well-known. (See, e.g., Amon et al., "Monoclonal Antibodies For Immunotargeting Of Drugs In Cancer Therapy," in *Monoclonal Antibodies And Cancer Therapy* (Reisfeld et al. eds., Alan R. Liss, Inc., 1985); Hellstrom et al., "Antibodies For Drug Delivery," in *Controlled Drug Delivery* (Robinson et al. eds., Marcel Deiker, Inc., 2nd ed. 1987); Thorpe, "Antibody Carriers Of Cytotoxic Agents In Cancer Therapy: A Review," in *Monoclonal Antibodies '84: Biological And Clinical Applications* (Pinchera et al. eds., 1985); "Analysis, Results, and Future Prospective of the Therapeutic Use of Radiolabeled Antibody In Cancer Therapy," in *Monoclonal Antibodies For Cancer Detection And Therapy* (Baldwin et al. eds., Academic Press, 1985); and Thorpe et al., 1982, *Immunol. Rev.* 62:119-58. See also, e.g., PCT publication WO 89/12624.)

Diagnostic Uses:

A further object of the invention relates to an anti-Axl antibody of the invention for diagnosing and/or monitoring a cancer disease and other diseases in which Axl levels are modified (increase or decrease).

In a preferred embodiment, antibodies of the invention may be labelled with a detectable molecule or substance, such as a fluorescent molecule, a radioactive molecule or any others labels known in the art as above described. For example, an antibody of the invention may be labelled with a radioactive molecule by any method known to the art. For example radioactive molecules include but are not limited radioactive atom for scintigraphic studies such as I123, I124, In111, Re186, Re188. Antibodies of the invention may be also labelled with a spin label for nuclear magnetic resonance (NMR) imaging (also known as magnetic resonance imaging, mri), such as iodine-123, iodine-131, indium-Ill, fluorine-19, carbon-13, nitrogen-15, oxygen-17, gadolinium, manganese or iron. Following administration of the antibody, the distribution of the antibody within the patient is detected. Methods for detecting distribution of any specific label are known to those skilled in the art and any appropriate method can be used. Some non-limiting examples include, computed tomography (CT), position emission tomography (PET), magnetic resonance imaging (MRI), fluorescence, chemiluminescence and sonography.

Antibodies of the invention may be useful for diagnosing and staging of cancer diseases associated with Axl overexpression (e.g., in radioimaging). Cancer diseases associated with Axl overexpression typically include but are not limited to squamous cell cancer, small-cell lung cancer, non-small cell lung cancer, gastric cancer, pancreatic cancer, glial cell tumors such as glioblastoma and neurofibromatosis, cervical cancer, ovarian cancer, liver cancer, bladder cancer, hepatoma, breast cancer, colon cancer, melanoma, colorectal cancer, endometrial carcinoma, salivary gland carcinoma, kidney cancer, renal cancer, prostate cancer, vulval cancer, thyroid cancer, hepatic carcinoma, sarcomas, hematological cancers (leukemias), astrocytomas, and various types of head and neck cancer or other Axl expressing or overexpressing hyperproliferative diseases.

Antibodies of the invention may be useful for diagnosing diseases other than cancers for which Axl expression is increased or decreased (soluble or cellular Axl form).

Typically, said diagnostic methods involve use of biological sample obtained from the patient. As used herein the term "biological sample" encompasses a variety of sample types obtained from a subject and can be used in a diagnostic or monitoring assay. Biological samples include but are not limited to blood and other liquid samples of biological origin, solid tissue samples such as a biopsy specimen or tissue cultures or cells derived therefrom, and the progeny thereof. For example, biological samples include cells obtained from a tissue sample collected from an individual suspected of having a cancer disease associated with Axl overexpression, and in a preferred embodiment from glioma, gastric, lung, pancreatic, breast, prostate, renal, hepatic and endometrial. Therefore, biological samples encompass clinical samples, cells in culture, cell supernatants, cell lysates, serum, plasma, biological fluid, and tissue samples.

In a particular embodiment, the invention is a method of diagnosing a cancer disease associated with Axl overexpression in a subject by detecting Axl on cells from the subject using the antibody of the invention. In particular, said method of diagnosing may comprise the steps consisting of:

(a) contacting a biological sample of a subject likely to suffer from a cancer disease associated with Axl overexpression with an antibody according to the invention in conditions sufficient for the antibody to form complexes with cells of the biological sample that express Axl;

(b) detecting and/or quantifying said complexes, whereby the detection of said complexes is indicative of a cancer disease associated with Axl overexpression.

In order to monitor the cancer disease, the method of diagnosing according to the invention may be repeated at different intervals of time, in order to determine if antibody binding to the samples increases or decreases, whereby it is determined if the cancer disease progresses or regresses.

In a particular embodiment, the invention is a method of diagnosing a disease associated with the expression or the overexpression of Axl or the decrease or increase of the soluble form of Axl, such as human immune disorders, thrombotic diseases (thrombosis and atherothrombosis), and cardiovascular diseases can be also diagnosed by the anti-Axl antibody of the invention.

Therapeutic Uses:

Antibodies, fragments or immunoconjugates of the invention may be useful for treating any disease associated with Axlexpression preferentially cancers. The antibodies of the invention may be used alone or in combination with any suitable agent.

1) anti-Axl antibody of the invention may be used as treatment of hyperproliferative diseases associated with Axl and or Gas6 expression, overexpression or activation. There are no particular limitations on the tumor tissues, and examples include squamous cell cancer, small-cell lung cancer, non-small cell lung cancer, gastric cancer, pancreatic cancer, glial cell tumors such as glioblastoma and neurofibromatosis, cervical cancer, ovarian cancer, liver cancer, bladder cancer, hepatoma, breast cancer, colon cancer, melanoma, colorectal cancer, endometrial carcinoma, salivary gland carcinoma, kidney cancer, renal cancer, prostate cancer, vulval cancer, thyroid cancer, hepatic carcinoma, sarcomas, hematological cancers (leukemias), astrocytomas, and various types of head and neck cancer. More preferable cancers are glioma, gastric, lung, pancreatic breast, prostate, renal, hepatic and endometrial. 2) anti-Axl antibody of the invention are potential activators of the innate immune response and may be used in the treatment of human immune disorders, such as sepsis, may be used as adjuvants for immunization such as for vaccine and may be used as anti-infectious agents (against bacteria, virus, parasites)3) anti-Axl antibody of the invention may protect or treat thrombotic diseases such as venous and arterial thrombosis and atherothrombosis 4) anti-Axl antibody of the invention may protect, prevent or treat cardiovascular diseases 5) anti-Axl antibody of the invention may prevent or inhibit the entry of viruses such as Lassa and Ebola viruses and may be used to treat viral infections In each of the embodiments of the treatment methods described herein, the anti-Axl monoclonal antibody or anti-Axl monoclonal antibody-drug conjugate is delivered in a manner consistent with conventional methodologies associated with management of the disease or disorder for which treatment is sought. In accordance with the disclosure herein, an effective amount of the antibody or antibody-drug conjugate is administered to a subject in need of such treatment for a time and under conditions sufficient to prevent or treat the disease or disorder.

Thus, an object of the invention relates to a method for treating a disease associated with the expression of Axl comprising administering a subject in need thereof with a therapeutically effective amount of an antibody, fragment or immunoconjugate of the invention.

In the context of the invention, the term "treating" or "treatment", as used herein, means reversing, alleviating, inhibiting the progress of, or preventing the disorder or condition to which such term applies, or one or more symptoms of such disorder or condition.

According to the invention, the term "patient" or "patient in need thereof" is intended for a human affected or likely to be affected with disease associated with overexpression of Axl.

By a "therapeutically effective amount" of the antibody of the invention is meant a sufficient amount of the antibody to treat said cancer, at a reasonable benefit/risk ratio applicable to any medical treatment. It will be understood, however, that the total daily usage of the antibodies and compositions of the present invention will be decided by the attending physician within the scope of sound medical judgment. The specific therapeutically effective dose level for any particular patient will depend upon a variety of factors including the disorder being treated and the severity of the disorder; activity of the specific antibody employed; the specific composition employed, the age, body weight, general health, sex and diet of the patient; the time of administration, route of administration, and rate of excretion of the specific antibody employed; the duration of the treatment; drugs used in combination or coincidental with the specific antibody employed; and like factors well known in the medical arts. For example, it is well known within the skill of the art to start doses of the compound at levels lower than those required to achieve the desired therapeutic effect and to gradually increase the dosage until the desired effect is achieved.

In certain embodiments, an anti-Axl monoclonal antibody or antibody-drug conjugate is used in combination with a second agent for treatment of a disease or disorder. When used for treating cancer, an anti-Axl monoclonal antibody or antibody-drug conjugate of the present invention may be used in combination with conventional cancer therapies such as, e.g., surgery, radiotherapy, chemotherapy, or combinations thereof. In certain aspects, other therapeutic agents useful for combination cancer therapy with an anti-Axl antibody or antibody-drug conjugate in accordance with the present invention include anti-angiogenic agents. In some aspects, an antibody or antibody-drug conjugate in accordance with the present invention is co-administered with a cytokine (e.g., a cytokine that stimulates an immune response against a tumor).

In some embodiments, an anti-Axl monoclonal antibody or antibody-drug conjugate as described herein is used in combination with a tyrosine kinase inhibitor (TKI).

In some embodiments, an anti-Axl monoclonal antibody or antibody-drug conjugate as described herein is used in combination with another therapeutic monoclonal antibody (mAb). Trastuzumab (Herceptin, Roche), Bevacizumab (Avastin, Roche) and Cetuximab (Erbitux, Merck) are three such mAb that have been approved. Other mAb include, but are not limited to: Infliximab (Remicade, Johnson&Johnson), Rituximab (Rituxan, Roche), Adalimumab (Humira, Abbott) and Natalizumab (Tysabri, Biogen).

Pharmaceutical Compositions:

For administration, the anti-Axl monoclonal antibody or antibody-drug conjugate is formulated as a pharmaceutical composition. A pharmaceutical composition comprising an anti-Axl monoclonal antibody or antibody-drug conjugate can be formulated according to known methods to prepare pharmaceutically useful compositions, whereby the therapeutic molecule is combined in a mixture with a pharmaceutically acceptable carrier. A composition is said to be a "pharmaceutically acceptable carrier" if its administration can be tolerated by a recipient patient. Sterile phosphate-buffered saline is one example of a pharmaceutically acceptable carrier. Other suitable carriers are well-known to those in the art. (See, e.g., Gennaro (ed.), Remington's Pharmaceutical Sciences (Mack Publishing Company, 19th ed. 1995)) Formulations may further include one or more excipients, preservatives, solubilizers, buffering agents, albumin to prevent protein loss on vial surfaces, etc.

The form of the pharmaceutical compositions, the route of administration, the dosage and the regimen naturally depend upon the condition to be treated, the severity of the illness, the age, weight, and sex of the patient, etc.

The pharmaceutical compositions of the invention can be formulated for a topical, oral, parenteral, intranasal, intravenous, intramuscular, subcutaneous or intraocular administration and the like.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The doses used for the administration can be adapted as a function of various parameters, and in particular as a function of the mode of administration used, of the relevant pathology, or alternatively of the desired duration of treatment.

To prepare pharmaceutical compositions, an effective amount of the antibody may be dissolved or dispersed in a pharmaceutically acceptable carrier or aqueous medium.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

An antibody of the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The preparation of more, or highly concentrated solutions for direct injection is also contemplated, where the use of DMSO as solvent is envisioned to result in extremely rapid penetration, delivering high concentrations of the active agents to a small tumor area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

The antibodies of the invention may be formulated within a therapeutic mixture to comprise about 0.0001 to 1.0 milligrams, or about 0.001 to 0.1 milligrams, or about 0.1 to 1.0 or even about 10 milligrams per dose or so. Multiple doses can also be administered.

In addition to the compounds formulated for parenteral administration, such as intravenous or intramuscular injection, other pharmaceutically acceptable forms include, e.g. tablets or other solids for oral administration; time release capsules; and any other form currently used.

In certain embodiments, the use of liposomes and/or nanoparticles is contemplated for the introduction of antibodies into host cells. The formation and use of liposomes and/or nanoparticles are known to those of skill in the art.

Nanocapsules can generally entrap compounds in a stable and reproducible way. To avoid side effects due to intracellular polymeric overloading, such ultrafine particles (sized around 0.1 µm) are generally designed using polymers able to be degraded in vivo. Biodegradable polyalkyl-cyanoacrylate nanoparticles that meet these requirements are contemplated for use in the present invention, and such particles may be are easily made.

Liposomes are formed from phospholipids that are dispersed in an aqueous medium and spontaneously form multilamellar concentric bilayer vesicles (also termed multilamellar vesicles (MLVs)). MLVs generally have diameters of from 25 nm to 4 µm. Sonication of MLVs results in the formation of small unilamellar vesicles (SUVs) with diameters in the range of 200 to 500 Å, containing an aqueous solution in the core. The physical characteristics of liposomes depend on pH, ionic strength and the presence of divalent cations.

Kits:

Finally, the invention also provides kits comprising at least one antibody of the invention. Kits containing antibodies of the invention find use in detecting Axl expression (increase or decrease), or in therapeutic or diagnostic assays. Kits of the invention can contain an antibody coupled to a solid support, e.g., a tissue culture plate or beads (e.g., sepharose beads). Kits can be provided which contain antibodies for detection and quantification of Axl in vitro, e.g. in an ELISA or a Western blot. Such antibody useful for detection may be provided with a label such as a fluorescent or radiolabel.

The invention will be further illustrated by the following figures and examples. However, these examples and figures should not be interpreted in any way as limiting the scope of the present invention.

FIGURES LEGENDS

Figure 1:
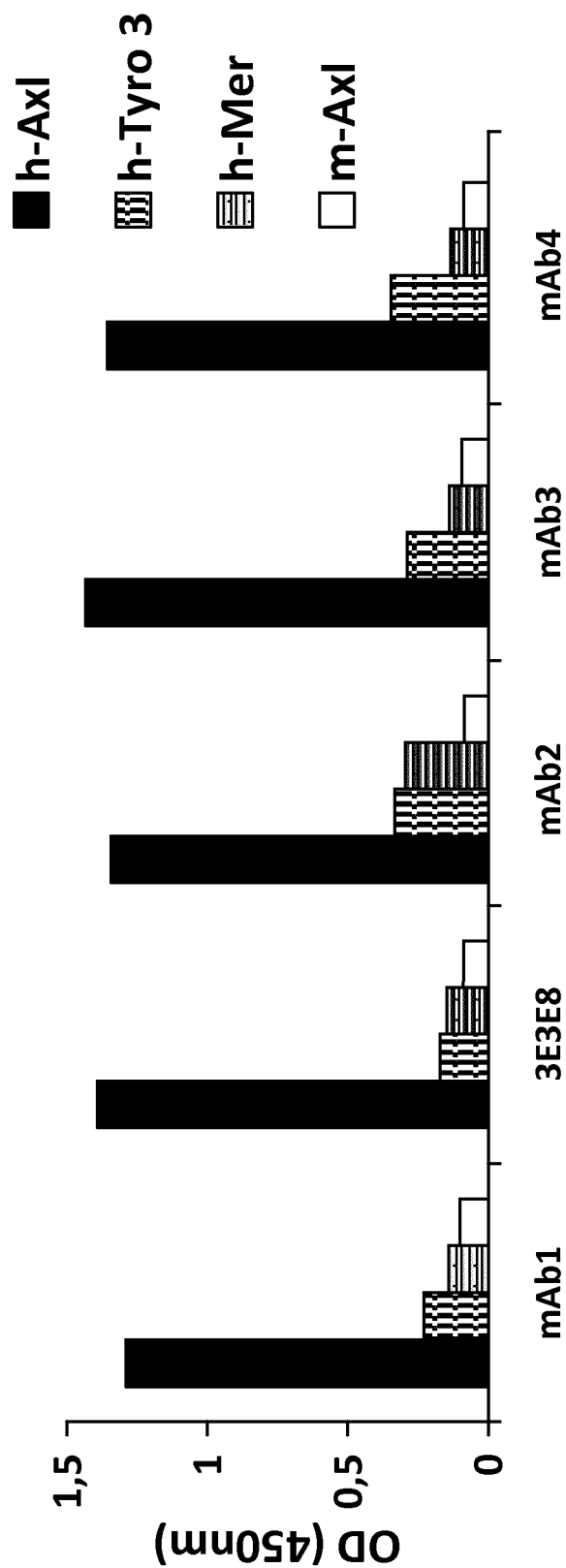

FIG. 1: ELISA experiments to investigate the affinity and the specificity of mouse monoclonal antibodies against hAxl. Plates coated with human Axl-Fc (h-Axl), mouse Axl-Fc (m-Axl) or human Mer-Fc (h-Mer), Tyro-3-Fc (h-Tyro-3) were incubated with anti-Axl antibodies (mAb1, mAb2, mAb3, mAb4 or 3E3-E8). After washing, HRP-conjugated anti-mouse IgG was added. 3E3-E8 doesn't cross-react with h-Tyro-3 or h-Mer or m-Axl.

Figure 2:
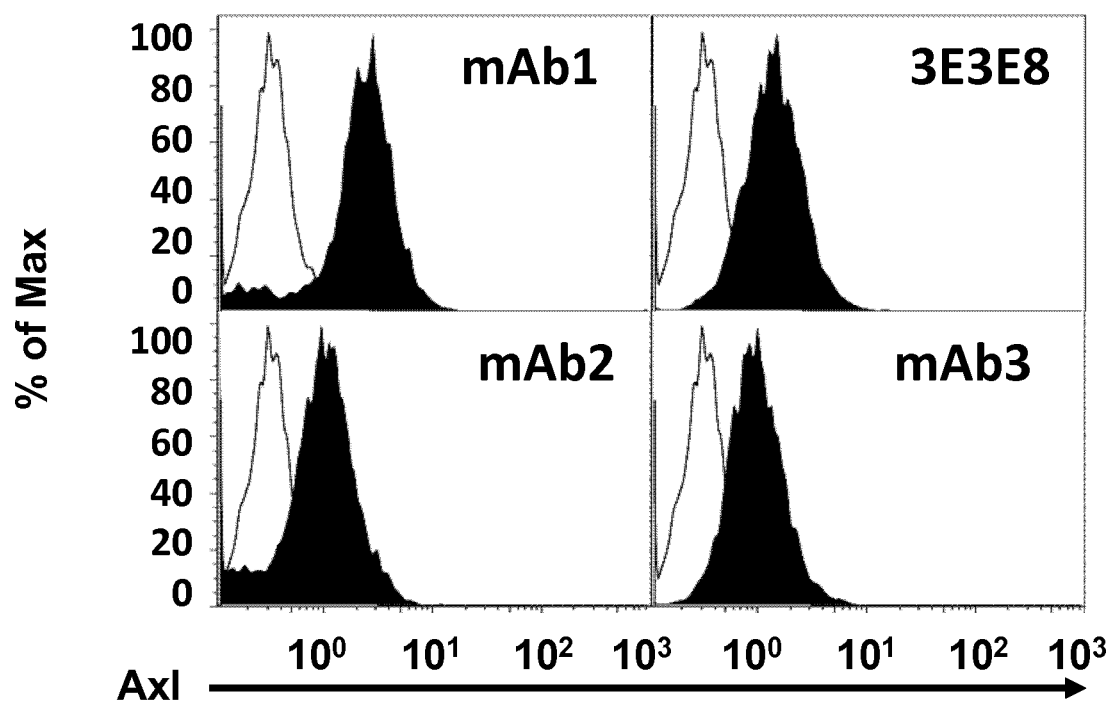

FIG. 2: Flow cytometry analysis of cell surface Axl in A549. A549 were stained with monoclonal anti-Axl antibodies (mAb1, mAb2, mAb3, mAb4 or 3E3-E8) and fluorescein-conjugated anti-mouse IgG. Staining with 3E3-E8 results in a shift by one order of magnitude and demonstrates Axl overexpression on the surface of these cells.

FIG. 3: Affinity measurement of 3E3-E8 in the presence or not of Gas6 using BIAcore. (A) Without Gas6, the association rates ($k_a$) and dissociation rates ($k_d$) were calculated using a simple one-to-one Langmuir binding model. The equilibrium dissociation constant ($K_D$) was derived as the $k_d/k_a$ ratio. 3E3-E8 binds to human Axl with high affinity, with a $K_D$ of about 1.6 nM. (B) 3E3-E8 doesn't block the binding of ligand Gas6 to Axl.

Figure 4:
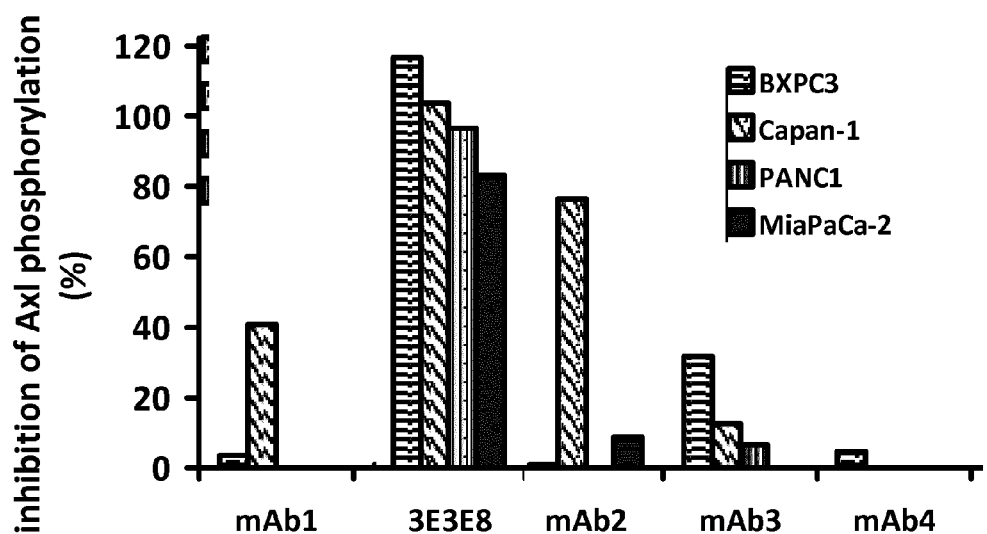

FIG. 4: ELISA experiments to investigate the effects of 3E3-E8 mAb on Axl receptor phosphorylation. BXPC3, Capan-1, PANC1 and MIAPaCa-2 pancreatic cancer cells were serum-starved, pre-incubated with mouse anti-Axl antibodies and treated with Gas6 ligand. Cell lysates were transferred to PathScan® Phospho-Axl (PanTyr) Sandwich ELISA plates (RD Systems, Minneapolis, Minn.). Compared with other antibodies, 3E3-E8 was able to block or significantly reduce Gas6-mediated Axl activation in the four cell lines as indicated by decreased Axl phosphorylation levels in Gas6-stimulated cells.

Figure 5:
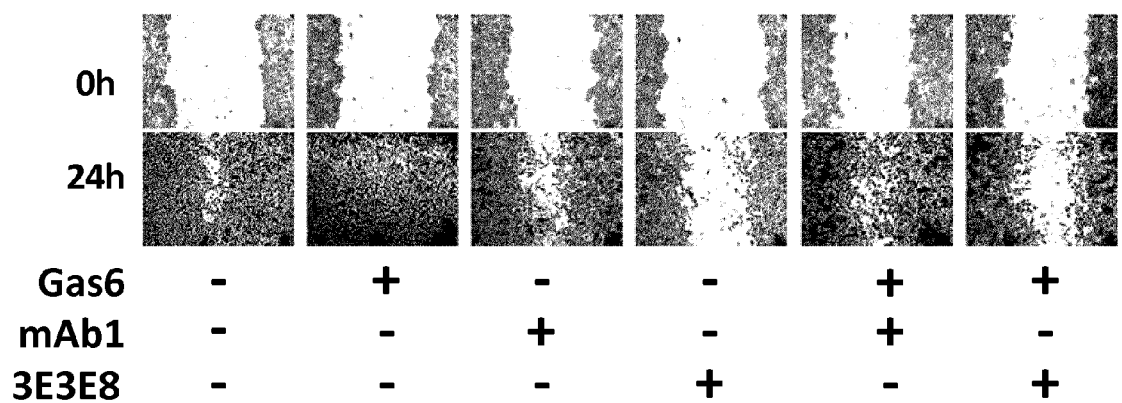

FIG. 5: Wound healing/scratch assay to investigate the effects of mouse anti-Axl antibodies on cell migration and proliferation. After grown to confluency, A549 cells were starved and wounded with a pipette tip. 3E3E8 mouse anti-Axl reduced the repopulation of the cleared area more significantly than the mAb1, even though the cells were treated with Gas6.

Figure 6:
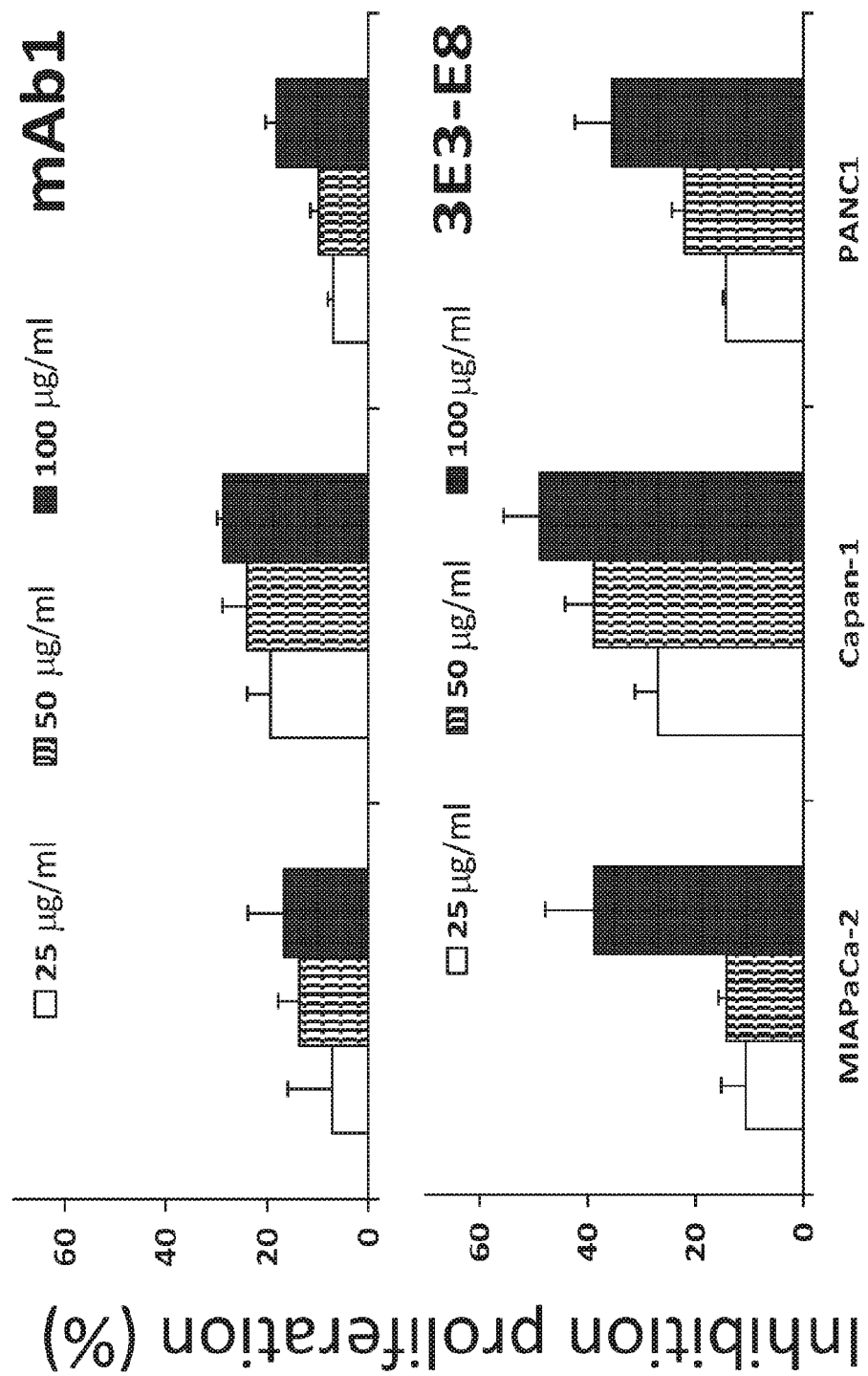

FIG. 6: Cell viability assay to investigate the anti-proliferative efficacy of anti-Axl 3E3-E8. Capan-1, PANC1 and MIAPaCa-2 pancreatic cancer cells were grown in medium and treated at the indicated concentrations of mAb1 or 3E3-E8 for 5 days. Cell viability was measured by MTS. 3E3-E8 inhibits more the growth of all tested cell lines than mAb1 and the percentage of inhibition is concentration-dependent.

Figure 7A:
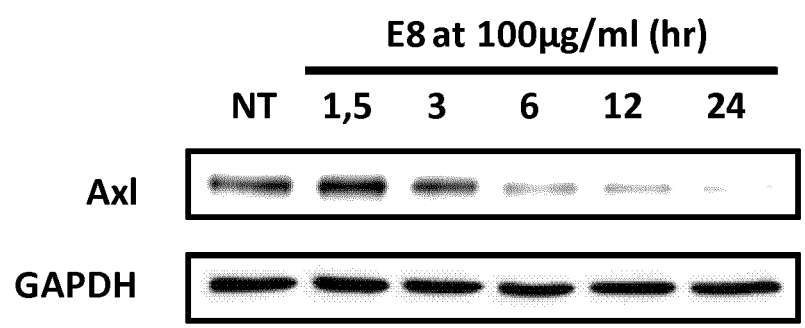
Figure 7B:
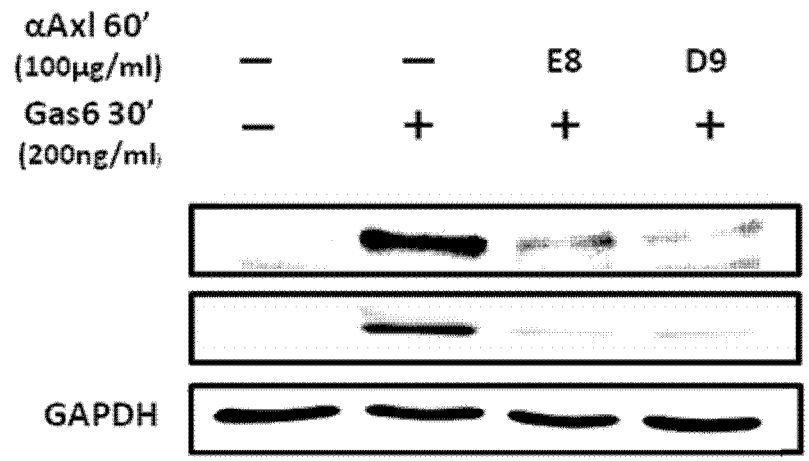

FIG. 7: monoclonal anti-Axl 3E3-E8 antibody induces a rapid down-regulation of Axl receptor and inhibits Akt pathway. Panc1-cells were incubated with 100 µg/ml of mAb 3E3-E8 for different time. Cells were lyzed and total protein were used to detect by western-blot. As shown in FIG. 7A, mAb 3E3-E8 rapidly down-regulates the expression of Axl receptor in Panc1 cells. After one hour incubation with mAb 3E3-E8, cells were incubated 30 minutes with Gas6 and the presence of Axl receptor phosphorylation on tyrosine 702 (Axl activation) and phosphorylation of Akt on serine 473 (Akt activation) was analyzed by western blot. As shown in FIG. 7B, mAb 3E3-E8 incubation leads to a decrease in the Gas6-induced phosphorylation of Axl and Akt proteins.

FIG. 8: Xenograft models to investigate the effects of mouse anti-Axl antibodies on human triple negative breast cancer and human pancreatic cancer in nude mice. MDA-MB-231 (triple negative breast cancer cells) or MIAPaca-2, BXPC3 (pancreatic cancer cells) were implanted into the right flank of athymic nude mice. Animals received 300 µg/injection of the mouse anti-Axl antibodies. During the treatment, the growth of tumors was monitored once weekly with a calliper. 3E3-E8 reduced more the overall growth of pancreatic and triple negative tumors in nude mice than mAb1 (A, B, C) and significantly increase the overall survival in comparison with vehicle or Gemcitabine in pancreatic BXPC3 xenografted mice (D). On explanted MIAPaca-2 xenografts tumors which received two injections, a drastic down-expression of Axl receptor by mAb 3E3-E8 is also observed (E)

FIG. 9: Sequence of the hAxl-hFc and localization/sequence of the epitope of anti-Axl mAb 3E3-E8The epitope of anti-Axl antibody 3E3-E8 was identified by limited proteoloysis assays using either Trypsin or GIuC proteases and MALDI mass spectrometry analysis. The figure shows the composition of the antigen (hAxl-hFc, SEQ ID NO:11) used in this experiment which is composed of amino acids 33-440 of the extracellular domain of Axl fused to the Fc part of human IgG1 and histidine Tag. Each immunoqlobulin like domains and fibronectin 3 domains of the Axl protein is indicated on the sequence. mAb 3E3-E8binds to two peptides (conformational epitope) localized in the first (SEQ ID NO:9) and the second (SEQ ID NO:10) fibronectin domains (sequences are framed in the sequence of the protein and detailed in the table).

Figure 10:
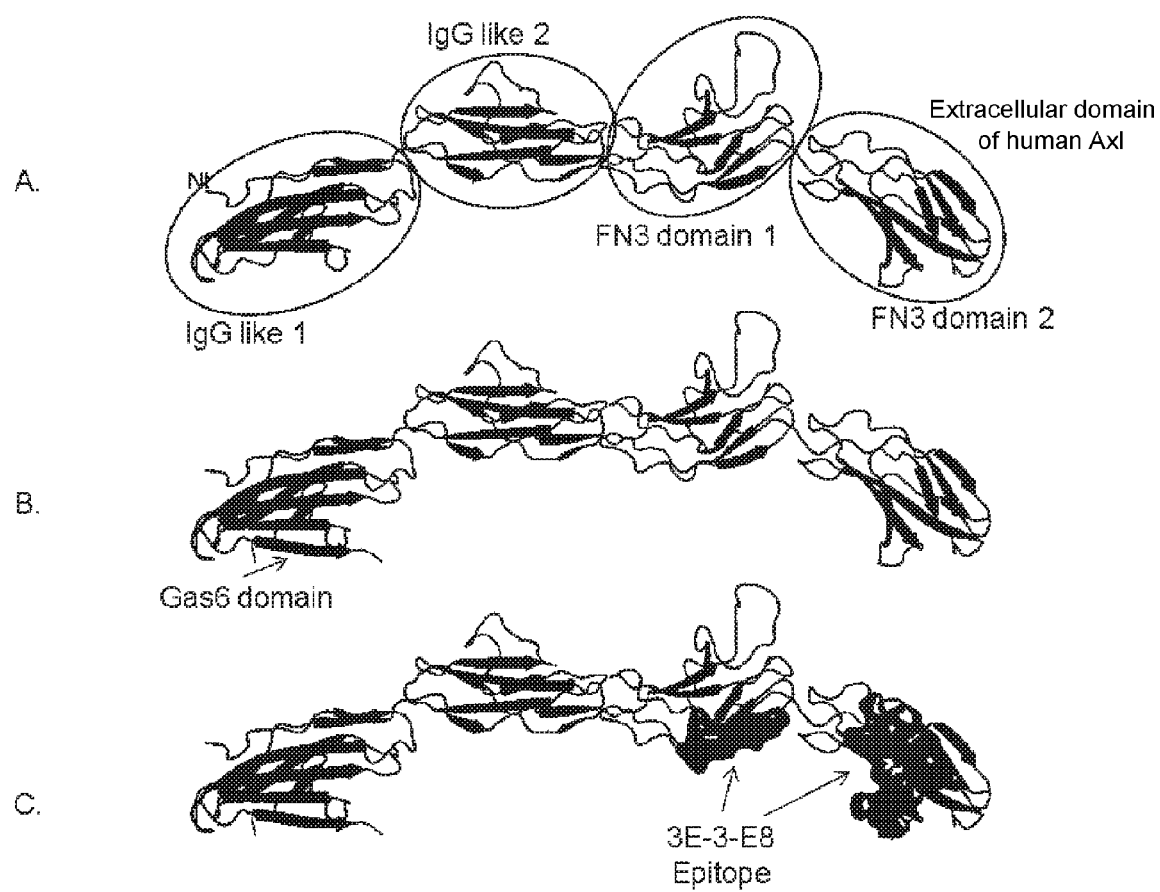

FIG. 10: Representation of a model of the ectodomain of human Axl and localization of the epitope of anti-Axl mouse monoclonal antibody 3E3-E8 and Gas6 binding domain. FIG. 10A displays a cartoon-type representation of the model of the whole extracellular domain of human Axl with all four domains labeled. In FIG. 10B, fragment from amino acid 305 to 315 of Gas6 was added as a light-grey β sheet, illustrating the Gas6 binding domain within the Immunoglobulin-like domain 1 of Axl. Finally, FIG. 10C exhibits the 3E3-E8 epitope within the fibronectin type III domains 1 and 2 as grey surfaces. It confirms first that the two parts of the epitope are localized on the outside surface of each domain. Secondly, the FIG. 10C illustrates also that the interaction site of Gas6 and the epitope are situated far from each other on the human Axl ectodomain.

EXAMPLE

Example 1

Generation of Mouse Anti-Axl Monoclonal Antibody

Monoclonal antibodies against Axl were developed by sequential immunization of Balb/c mice. Balb/c mice were hyperimmunized with human Axl extracellular domain (hAxlECD) fused to human Fc domain (hAxl-hFc protein; R&D system). Balb/c mice were subcutaneously injected with 10 µg of soluble hAxl-hFc on days 0, 14 and 28 in the presence of adjuvant, Freund's complete (first injection) or incomplete (second and third injections). Spleen cells from mice were fused with mouse myeloma cells (PX63.Ag8.653; ATCC, Rockville, Md.) using a previously described protocol (Salhi et al. Biochem. J. 2004). Cells were cultured in plates ($10^5$ per well) with HAT media for hybridoma selection. After 12 days, the supernatants were harvested and screened for Axl binding specificity (hAxl-hFc or hFc alone) by direct enzyme-linked immunosorbent assay (ELISA). Eight positive clones, showing the highest immunobinding after the second round of subcloning by limiting dilution, were expanded for large scale in vitro production of mAb. Conditioned supernatants were purified by Protein G affinity chromatography.

Example 2

Mouse Anti-Axl Monoclonal Antibodies do not Cross React with Mouse Axl or Other Members of the Human Tam Receptor Family

Example 2.1

Mouse Anti-Axl Monoclonal Antibodies do not Cross React with Mouse Axl or Other Members of the Human TAM Receptor Family as Determined by ELISA Briefly, hAxl-hFc coated plates were saturated with 1% bovine serum albumin (BSA) PBS, 0.1% Tween 20 (PBST).

For cross reaction assay, coated plates were incubated with human Axl-Fc (h-Axl), mouse Axl-Fc (m-Axl) or human Mer-Fc (h-Mer), Tyro-3-Fc (h-Tyro-3) for 1 hour at 37° C. and washed four times in PBST. Plates were incubated with anti-Axl mAbs (2 hours at 37° C.) and washed four times in PBST. Plates were incubated with HRP-conjugated anti-mouse IgG (Sigma) at a 1:2000 dilution in PBST, 1% BSA (1 hour at 37° C.). Finally, an ortho-phenylenediamine solution (Sigma) was added for 30 min at room temperature in the dark and the absorbance was measured at 450 nm.

The specificity against h-Axl, in a dose-specific manner, of the ten anti-hAxlECD mAbs selected was demonstrated (FIG. 1).

Example 2.2

Mouse Anti-Axl Monoclonal Antibody Binds Specifically Axl-Expressing Cells as Determined by FACS The ability of mouse anti-Axl monoclonal antibodies of the invention to specifically recognize Axl expressing cells was determined by FACS using standard techniques. Briefly, A549 cells (ATCC number: CCL-185) were harvested, stained with purified mouse anti-Axl monoclonal antibodies of the invention at 4° C. for 1 hour, washed three times in PBS-BSA 0.1%, and then stained with fluorescein-conjugated anti-mouse IgG (1:50) (Sigma) at 4° C. in the dark for 45 min. Samples were analyzed on EPICS flow cytometer (Beckman-Coulter, Fullerton, Calif.). As shown in FIG. 2, mouse anti-Axl monoclonal antibodies of the invention bound specifically Axl expressing-A549 cells.

Example 2.3

Affinity Measurement of Mouse Anti-Axl Monoclonal Antibody Evaluated by BIACore For binding affinity determination of anti-Axl antibodies, a surface Plasmon Resonance measurement with a BIAcore-3000 instrument was used (BIACORE AB, Uppsala, Sweden). Experiments were performed at the facilities from the platform of Proteomic Imaging and Molecular Interactions (M. Pugniere) located in the laboratory. To measure the affinity between anti-Axl antibodies and the hAxl-hFc, mouse anti-Axl monoclonal antibodies were captured by CM5 biosensor chips coated with hAxl-hFc (using an amine coupling kit (BIAcore AB)). For measurement of kinetics, various concentrations of anti-Axl mAb (from 2 to 133 nM) in 10 mM HEPES, 150 mM NaCl, pH 7.4, 0.005% surfactant P20 buffer were injected at 25° C. with a flow rate of 50 µl/min. Association rates ($k_a$) and dissociation rates ($k_d$) were calculated using a simple one-to-one Langmuir binding model (BIAcore Evaluation Software version 3.2). The equilibrium dissociation constant ($K_D$) was calculated as the $k_a/k_d$ ratio. As indicated (FIG. 3A), 3E3-E8 showed a $K_D$ of $1.6 \times 10^{-9}$M.

Example 3

Mouse Anti-Axl Monoclonal Antibody does not Block the Binding of Gas6

For competition study, a saturating concentration of Gas6 (625 nM) was injected on CM5 biosensor chips coated with hAxl-hFc (using an amine coupling kit (BIAcore AB)). Mouse anti-Axl monoclonal antibody (666 nM) was injected without removing Gas6. The same experiment was performed injecting firstly the mouse anti-Axl monoclonal antibody (666 nM) and secondly Gas6 (625 nM). Results showed that 3E3-E8 did not compete with Gas6 ligand for hAxlECD (FIG. 3B).

Example 4

Mouse Anti-Axl Monoclonal Antibody of the Invention Inhibits Ligand Induced Axl Phosphorylation In Vitro ELISA experiments were performed in order to investigate whether the mouse anti-Axl monoclonal antibody of the invention was able to block ligand Gas6-induced phosphorylation of Axl. In brief, BXPC3 (ATCC number: CRL-1687), Capan-1 (ATCC number: HTB-79), PANC1 (ATCC number: CRL-1469) and MIAPaCa-2 (ATCC number: CRL-1420) cells were seeded in normal growth medium in flat-bottom 6 well plates. The next day, growth medium was replaced by serum-free medium to starve cells over night for 24 hours. Cells were pre-incubated with 100 µg/mL of purified mouse monoclonal anti-Axl of the invention, and then treated with or without 250 ng/mL Gas6 incubated with Gas6 for 30 min at 37° C. Afterwards, medium was removed, cells were lysed in 50 µL of lysis buffer (20 mM Tris pH 7.5, 150 mM NaCl, 1.5 mM $MgCl_2$, 1 mM EDTA, 1% Triton X-100 (v/v), 10% glycerol (v/v), 100 mM sodium fluoride, 0.1 mM phenylmethylsulfonyl fluoride, 1 mM sodium orthovanadate (Sigma)) supplemented with phosphatase and protease inhibitors (Roche Diagnostics, Meylan, France) for 30 min. Cell debris were removed by centrifugation and the protein concentrations were determined by Bradford colorimetric reaction. The PathScan® Phospho-Axl (PanTyr) Sandwich ELISA Kit (RD Systems, Minneapolis, Minn.) was used as described by the manufacturer for the detection of phospho-Axl level measuring absorbance at 450 nm in a colorimetric assay.

As shown in FIG. 4, mAb 3E3-E8 strongly inhibited Gas6 ligand-induced Axl phosphorylation in all pancreatic cancer cell lines. Other mAbs did not or slightly inhibit Gas6 ligand-induced Axl phosphorylation in all pancreatic cancer cell lines.

Example 5

Mouse Monoclonal Antibody Anti-Axl of the Invention Inhibits Cell Migration

A wound healing assay was performed observing the healing process in which the cells on the edges of the artificial wound migrate toward the wound area. A549 cells were cultured to confluence or near confluence (>90%) in 24 well plates. A wound field was created at the center of the well using a sterile pipette tip. Migratory cells are able to extend protrusions and ultimately invade and close the wound field. The cells were rinsed very gently with PBS and incubated with purified mouse anti-Axl monoclonal antibodies of the invention (100 µg/mL) with or without 100 µg/mL of Gas6. Cell migration rate was determined 24 hours after treatment using microscopic imaging. As shown in FIG. 5, mAb 3E3-E8 strongly inhibited cell migration as healing area was still visible in contrast to mAb1 or Gas6 treated cells.

Example 6

Mouse Monoclonal Antibody Anti-Axl of the Invention Inhibits Cell Proliferation

MIAPaca-2, Capan-1 and PANC1 pancreatic cancer cells were seeded at 4000 cells/well in 96-well plates and treated with mouse anti-Axl monoclonal antibodies (25, 50 or 100 µg/mL) for 5 days. Cell proliferation assays were carried out using the MTS assay (3-(4,5-dimethylthiazol-2-yl)-5-(3-carboxymethoxyphenyl)-2-(4-sulfophenyl)-2H-tetrazolium). MTS is reduced by cells into a formazan product that is soluble in tissue culture medium. The absorbance of the formazan at 490 nm was measured using a spectrophotometer. As shown in FIG. 6, mAb 3E3-E8 strongly inhibited the proliferation of pancreatic cells while a slight inhibition was observed with the other Axl-specific antibody (mAb1).

Example 7

The Mouse Anti-Human Axl Monoclonal Antibody of the Invention Down-Regulates Axl Expression and Inhibits Akt Pathway To decipher the mechanism involved in the inhibition of cell migration and Axl phosphorylation by mAb 3E3-E8, its direct effect on Axl receptor and downstream signaling pathways were analyzed (activation of Axl receptor by Gas6 ligand has been reported to induce several key signaling cascade notably the AKT pathway). The down-regulation of Axl receptor and the phosphorylation of Axl receptor and Akt were analyzed in a pancreatic cancer cell line (Panc-1 cells) treated with 3E3-E8 mAb by western blot.

Pancreatic cancer cell line, Panc-1 cells, were plated in 6 wells plate ($1 \times 10^6$ cells per well) and incubated with 100 ug/ml 3E3-E8 at 37° C. Cell lines harvested at different time point were lysed with buffer (150 mM NaCl, 10 mM TRIS pH7.4, 1 mM EDTA, 1% TRITON X100) containing 2 mM phenylmethylsulfonyl fluoride, 100 mM sodium fluorure, 10 mM sodium orthovanadate, and one tablet of complete protease inhibitor mixture (Sigma, St Louis, Mo.). After a resolving on 8%- or 10%-SDS-PAGE under reducing conditions, the proteins were transferred onto polyvinylidene difluoride membranes (Millipore, Bedford, Mass.) which were then saturated in PBS containing 0.1% Tween 20 and 5% nonfat dry milk. Membranes were incubated over-night at 4° C. with appropriate dilutions of anti-human-AXL (R&D systems), anti-phospho (Y702) Axl or anti-phospho (S473) Akt from Cell Signaling Technology. Immunoblots were normalized using an antibody directed to GAPDH (Millipore). Membranes were then incubated with appropriated horseradish peroxidase-conjugated secondary antibodies (Bio-Rad) and processed for ECL detection (Amersham) and analysis with G:BOX iChemi (Syngene).

When cells were treated with mAb 3E3-E8, Axl expression decreases rapidly after 90 minutes and is almost undetectable after 24 hours (FIG. 7A). An induction of the amount of phospho-Axl and phospho-Akt was observed when cells were stimulated with Gas6. Both signals were dramatically inhibited by pre-treatment with mAb 3E3-E8 (FIG. 7B).

Example 8

Figure 8A:
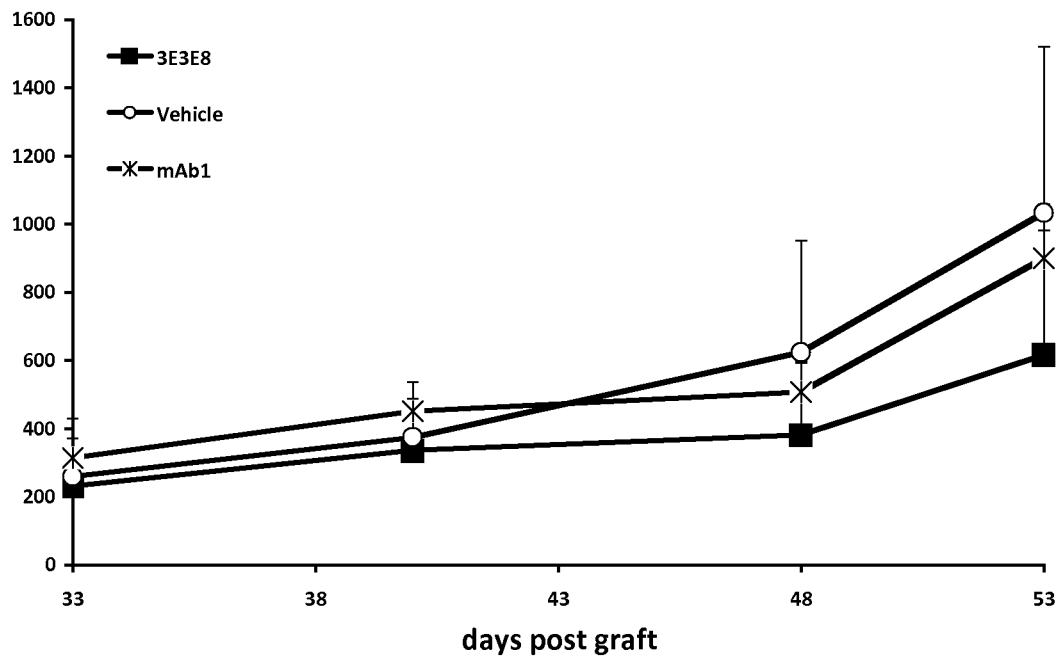
Figure 8B:
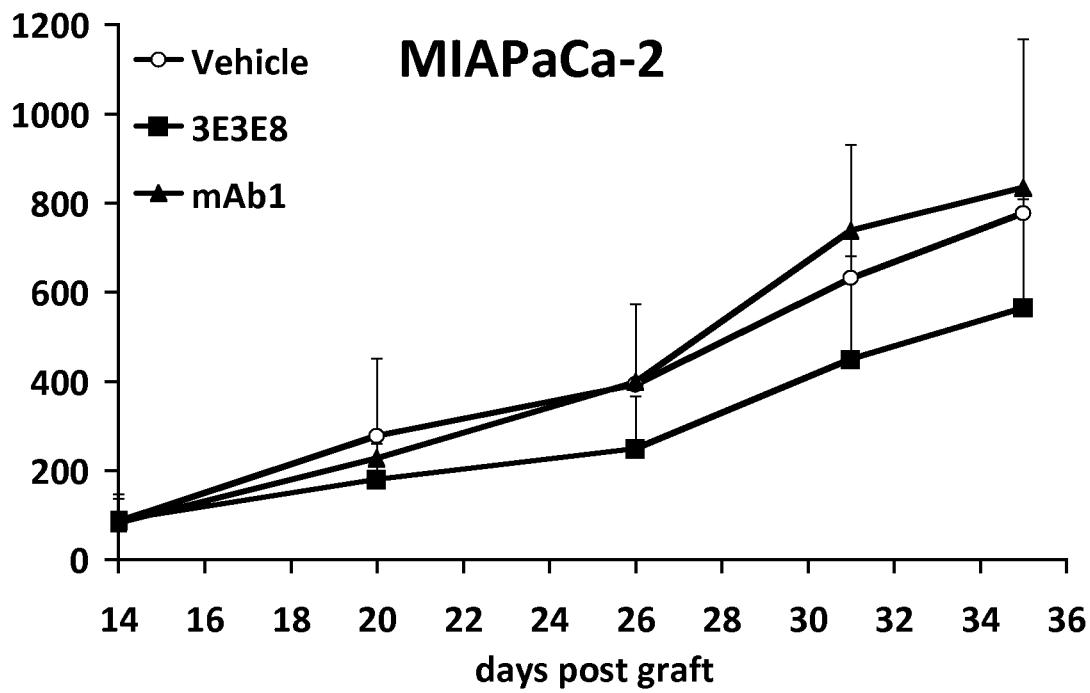
Figure 8C:
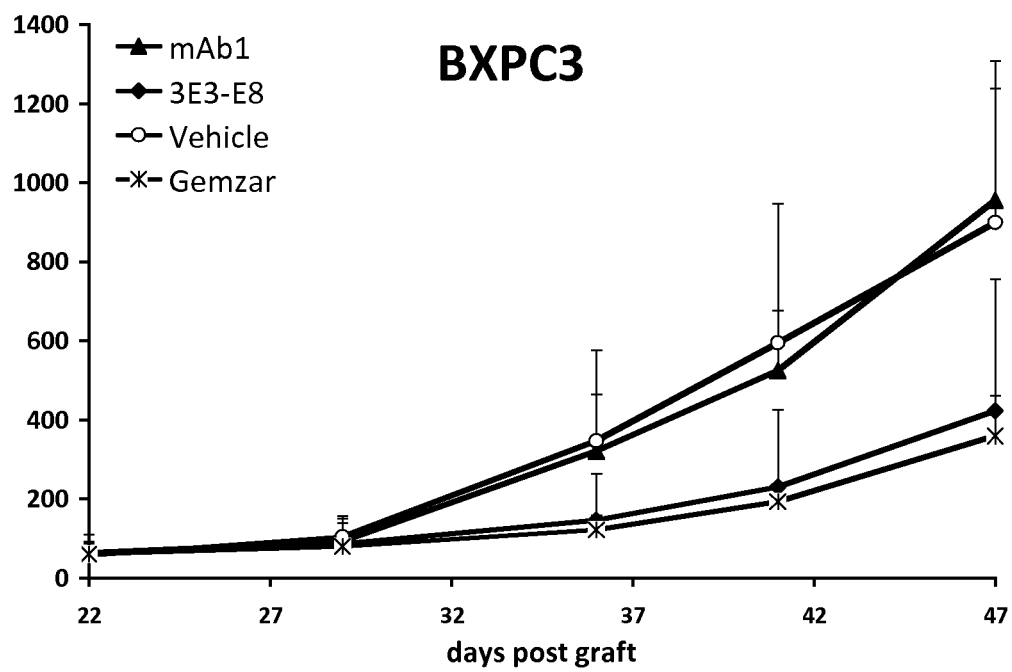
Figure 8D:
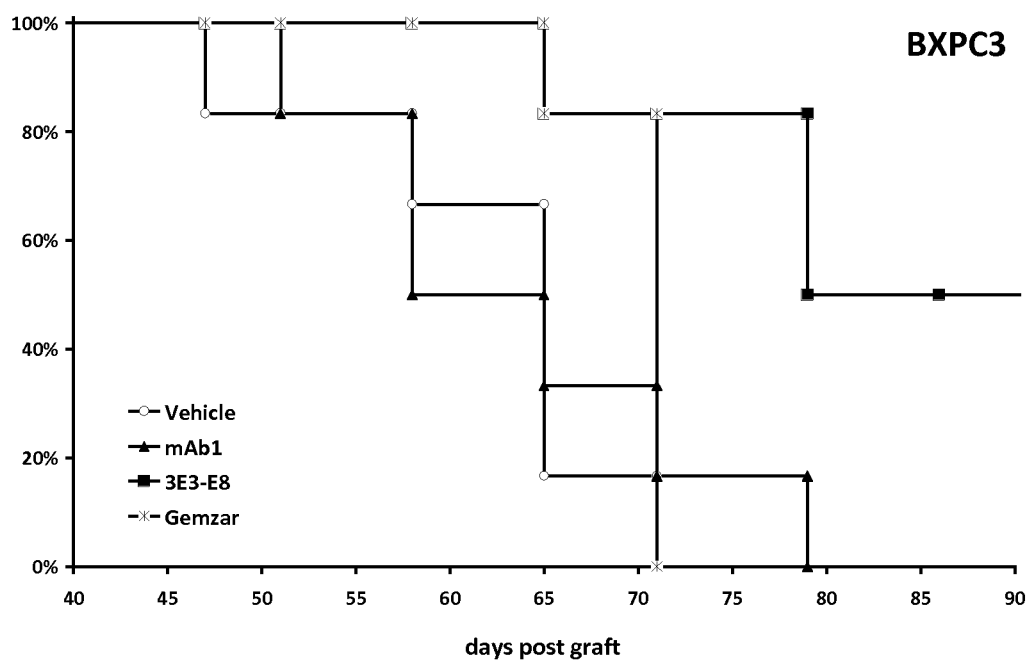

The Mouse Anti-Human Axl Monoclonal Antibody of the Invention Reduces Human Triple Negative Breast Cancer and Pancreatic Cancer Growth In Vivo Associated with the Down-Regulation of Axl Receptor All in vivo experiments were performed in compliance with the French guidelines for experimental animal studies (Agreement no. C34-172-27). Six-week old female athymic nude mice were purchased from Harlan. Triple-negative breast cancer cells ($5 \times 10^6$; MDA-MB-231; ATCC number: HTB-26) or pancreatic carcinoma cells ($3.5 \times 10^6$, BXPC3; $5 \times 10^6$, MIAPaCa-2) were implanted into right flank of athymic nude mice. Tumor-bearing mice were randomized in different treatment groups when tumors reached an approximate volume of 100 mm$^3$. The mice were treated by intraperitoneal injections with vehicle (0.9% NaCl) or mouse anti-Axl monoclonal antibodies of the invention alone at 300 µg/injection (twice a week for 4 consecutive weeks) or with gemcitabine (GEMZAR). Tumor volume was measured weekly with a caliper. The results for BXPC3 were also expressed by a modified Kaplan-Meier survival curve, using the time taken for the tumor to reach a pre-defined volume of 2,000 mm$^3$. A median delay was defined as the time at which 50% of the mice had a tumor reaching the volume of 2,000 mm$^3$. Anti-hAxl mAb 3E3-E8, but not mAb1, decreased tumor growth of MDA-MB-231 and pancreatic xenografts (FIG. 8A, B, C). Modified Kaplan-Meier curve demonstrated a 15-days delay to reach 50% survival when mice were treated with 3E3E8 antibody, when compared to NaCl-treated mice (FIG. 8D).

Figure 8E:
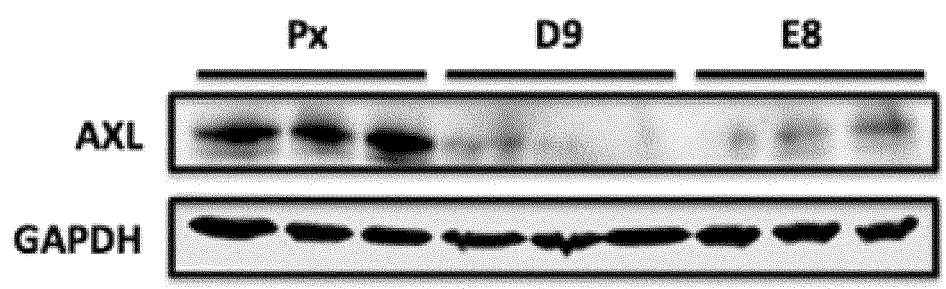

On another series of experiment, MIAPaca-2 xenografts treated with mAb 3E3-E8 or irrelevant murine IgG1 isotype mAb (Px) were explanted after two mAb treatment injections, and used for western-blot detection of Axl receptors (anti-Axl mAb, R&D systems) or GAPDH control protein (anti-GAPDH, Millipore). mAb 3E3-E8 treatment induced a marked decrease of Axl expression in tumors (FIG. 8E).

Example 9

The Epitope of the Mouse Anti-Human Axl Monoclonal Antibody is a Conformational Epitope Composed of 2 Peptides, One Localized in the Fibronectine 3 Domain 1 and One in the Fibronectine 3 Domain 2 of Human Axl To define the epitope structures, limited proteolysis assays of an immobilized antigen-antibody complex were performed. To map the 3E3-E8 epitope, the hAxl-hFc was affinity bound to the immobilized 3E3-E8 monoclonal antibody under physiological conditions. A series of proteolytic enzymatic cleavages (serine protease Trypsine and endoproteinase GluC) was then performed to remove hAxl-Fc residues that are unprotected by the 3E3-E8. After elution, the protected residues, i.e., the 3E3-E8 epitope, were identified based on their molecular weights, as determined by MALDI-MS analysis of the peptides that were affinity bound to the immobilized antibody.

The 3E3-E8 monoclonal antibody (250 µg) was coupled to ProMag Magnetics Microsphere PMC3N (Bangs Laboratories) 1 hour at room temperature according to the supplier's procedures. 50 µg of 3E3-E8 microbeads complex were incubated with 50 µg of the antigen hAxl-hFc (R&D system) and allowed to bind for 90 minutes at 4° C. Free antigen was removed by three washes with buffer. The immune complex of 3E3-E8 and hAxl-hFc was digested at 37° C. with 0.35 µg of Trypsin or GluC during 2h15min. The supernatant was separated by centrifugation (2000g, 4° C., 3 min) and discarded. The microbeads associated with 3E3-E8 and hAxl-hFc protected residues were washed three times with buffer. Dissociation was allowed to proceed for 40 min at room temperature using TFA (trifluoroacetic acid) 0.1%. Spectra were obtained by MALDI mass spectrometry (ABSCIEX MALDI 4800 with a Laser Nd/YAG at 355 nm, 200 Hz, 20 kV for the source of tension, extraction time of 250 ns) with the sum of 1500 laser shots. The matrix used for the sample was α-cyano-4-hydroxycinnaminic acid (CHCA) at 5 mg/mL. The sequence composition of the antigen hAxl-hFc (R&D system) and the epitope sequence of the 3E3-E8 antibody binds to a conformational 3D epitope composed of 2 peptides one positioned in the fibronectin type III domain 1 (sequence: "NLHLVSR" SEQ ID NO:9) and one positioned in the fibronectin type III domain 2 (sequence: "VLMDIGL-RQEVTLE" SEQ ID NO:10).

Example 10

The Epitope of the Mouse Anti-Human Axl Monoclonal Antibody is Exposed to the Accessible Solvent Surface Area and is Structurally Localized Far from the Interaction Site of Gas6

The extracellular domain model of the human Axl protein was constructed in 2 steps. First, the Immunoglobulin-like domains (domain 1 and 2) were extracted from the crystallographic structure available in the Protein Data Bank under the code 2C5D. This structure represents an Axl/Gas6 complex in which the two immunoglobulin-like domains of the Axl ectodomain are crosslinked by the first laminin G-like domain of Gas6. Unfortunately, the two fibronectin type III (FN3) domains of Axl have not been crystallized yet, and therefore needed to be modelized. The model was built by homology modeling using the 3D structure of FN3 tandem A77-A78 from the A chain of the human titin protein (PDB id: 3LPW) as template. After alignment, the sequences of the two proteins share an identity of 22.8%. Finally, the Immunoglobulin-like domains and the fibronectin type III domains were linked together between leucine 224 and proline 225 modifying dihedral angles in order to minimize the steric hindrance between the side chains of the two domains.

The epitope of the mouse anti-Axl antibody 3E3-E8 as well as the Gas6 binding domains were then identify on this model of the whole ectodomain of human Axl. This model demonstrates the specific localization of the two surface-localized antigenic sites recognized by 3E3-E8 on Axl (FIG. 10). This model demonstrated also that the 3E3-E8 epitope, composed of the 2 peptides (the first one in the FN3 domain 1 and the second one in the FN3 domain 2 of Axl), is localized far from ligand-binding site (Gas6-binding site which is localized in the IgG like domain 1) in accordance with the competition studies performed (example 3; FIG. 3B).

REFERENCES

Throughout this application, various references describe the state of the art to which this invention pertains. The disclosures of these references are hereby incorporated by reference into the present disclosure.

The invention claimed is:

1. A monoclonal antibody or an antigen binding fragment thereof having specificity to Axl comprising a heavy chain variable region comprising SEQ ID NO:2 in the H-CDR1 region, SEQ ID NO:3 in the H-CDR2 region and SEQ ID NO:4 in the H-CDR3 region; and a light chain variable region comprising SEQ ID NO:6 in the L-CDR1 region, SEQ ID NO:7 in the L-CDR2 region and SEQ ID NO:8 in the L-CDR3 region.

2. The monoclonal antibody according to claim 1 wherein the antibody comprises a heavy chain variable region of SEQ ID NO: 1.

3. The monoclonal antibody according to claim 1 wherein the antibody comprises a light chain variable region of SEQ ID NO: 5.

4. The monoclonal antibody according to claim 1 wherein the antibody comprises a heavy chain variable region of SEQ ID NO: 1 and a light chain variable region of SEQ ID NO: 5.

5. The monoclonal antibody according to claim 1 which is a chimeric antibody.

6. The monoclonal antibody according to claim 1 which is a humanized antibody.

7. The monoclonal antibody according to claim 1 which binds to the extracellular domain of Axl in the amino acid sequence set forth as SEQ ID NO:9 and in the amino acid sequence set forth as SEQ ID NO:10.

8. The antigen binding fragment of the monoclonal antibody of claim 1, wherein said fragment is selected from the group consisting of Fv, Fab, F(ab')2, Fab', dsFv, scFv, sc(Fv)2 and diabodies.

9. A nucleic acid sequence encoding the heavy chain and the light chain of the monoclonal antibody according to claim 1.

10. A vector comprising a nucleic acid according to claim 9.

11. A host cell comprising a nucleic acid according to claim 9.

12. A pharmaceutical composition comprising a monoclonal antibody or an antigen binding fragment thereof of claim 1.

13. A pharmaceutical composition comprising the monoclonal chimeric antibody according to claim 5, or antigen binding fragment thereof.

14. A method for treating cancer in a subject that comprises administering to the subject an anti-Axl monoclonal antibody or antigen binding fragment thereof according to claim 1.

15. A host cell comprising a vector according to claim 10.

16. The monoclonal antibody according to claim 1, which is a chimeric mouse/human antibody.

17. A pharmaceutical composition comprising the monoclonal humanized antibody according to claim 6, or an antigen binding fragment thereof.

* * * * *

SEQUENCE LISTING

<160> NUMBER OF SEQ ID NOS: 11

<210> SEQ ID NO 1
<211> LENGTH: 119
<212> TYPE: PRT
<213> ORGANISM: Artificial
<220> FEATURE:
<223> OTHER INFORMATION: VH chain

<400> SEQUENCE: 1

Gln Val Gln Leu Lys Glu Ser Gly Pro Gly Leu Val Ala Pro Ser Gln
1               5                   10                  15

Ser Leu Ser Ile Thr Cys Ser Val Ser Gly Phe Ser Leu Thr Asn Tyr
            20                  25                  30

Ala Val His Trp Val Arg Gln Pro Pro Gly Lys Gly Leu Glu Trp Leu
        35                  40                  45

Gly Val Ile Trp Ala Gly Gly Ser Thr Asn Tyr Asn Ser Ala Leu Met
    50                  55                  60

Ser Arg Leu Arg Ile Ser Lys Asp Asn Ser Lys Ser Gln Val Phe Phe
65                  70                  75                  80

Lys Met Asn Ser Leu Gln Thr Asp Asp Thr Ala Met Tyr Tyr Cys Ala
                85                  90                  95

Arg Tyr Tyr Gly Ser Ser Leu Tyr Pro Met Asp Tyr Trp Gly Gln Gly
            100                 105                 110

Thr Ser Val Thr Val Ser Ser
        115

<210> SEQ ID NO 2
<211> LENGTH: 5
<212> TYPE: PRT
<213> ORGANISM: Artificial
<220> FEATURE:
<223> OTHER INFORMATION: H-CDR1

<400> SEQUENCE: 2

Asn Tyr Ala Val His
1               5

<210> SEQ ID NO 3
<211> LENGTH: 16
<212> TYPE: PRT
<213> ORGANISM: Artificial
<220> FEATURE:
<223> OTHER INFORMATION: H-CDR2

<400> SEQUENCE: 3

Val Ile Trp Ala Gly Gly Ser Thr Asn Tyr Asn Ser Ala Leu Met Ser
1               5                   10                  15

<210> SEQ ID NO 4
<211> LENGTH: 11
<212> TYPE: PRT
<213> ORGANISM: Artificial
<220> FEATURE:
<223> OTHER INFORMATION: H-CDR3

<400> SEQUENCE: 4

Tyr Tyr Gly Ser Ser Leu Tyr Pro Met Asp Tyr
1               5                   10

<210> SEQ ID NO 5
<211> LENGTH: 112
<212> TYPE: PRT

```
<213> ORGANISM: Artificial
<220> FEATURE:
<223> OTHER INFORMATION: VL chain

<400> SEQUENCE: 5

Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Val Phe Thr Leu Arg Ile
65                  70                  75                  80

Ser Gly Val Glu Ala Glu Asp Val Gly Val Tyr Tyr Cys Met Gln His
                85                  90                  95

Leu Glu Tyr Pro Trp Thr Phe Gly Gly Gly Thr Glu Leu Glu Ile Lys
            100                 105                 110

<210> SEQ ID NO 6
<211> LENGTH: 16
<212> TYPE: PRT
<213> ORGANISM: Artificial
<220> FEATURE:
<223> OTHER INFORMATION: L-CDR1

<400> SEQUENCE: 6

Arg Ser Ser Lys Ser Leu Leu His Ser Asn Gly Asn Thr Tyr Leu Tyr
1               5                   10                  15

<210> SEQ ID NO 7
<211> LENGTH: 6
<212> TYPE: PRT
<213> ORGANISM: Artificial
<220> FEATURE:
<223> OTHER INFORMATION: L-CDR2

<400> SEQUENCE: 7

Arg Met Ser Asn Leu Ala
1               5

<210> SEQ ID NO 8
<211> LENGTH: 9
<212> TYPE: PRT
<213> ORGANISM: Artificial
<220> FEATURE:
<223> OTHER INFORMATION: L-CDR3

<400> SEQUENCE: 8

Met Gln His Leu Glu Tyr Pro Trp Thr
1               5

<210> SEQ ID NO 9
<211> LENGTH: 7
<212> TYPE: PRT
<213> ORGANISM: Artificial
<220> FEATURE:
<223> OTHER INFORMATION: FN3D1 epitope

<400> SEQUENCE: 9

Asn Leu His Leu Val Ser Arg
1               5
```

```
<210> SEQ ID NO 10
<211> LENGTH: 14
<212> TYPE: PRT
<213> ORGANISM: Artificial
<220> FEATURE:
<223> OTHER INFORMATION: FN3D2 epitope

<400> SEQUENCE: 10

Val Leu Met Asp Ile Gly Leu Arg Gln Glu Val Thr Leu Glu
 1               5                  10

<210> SEQ ID NO 11
<211> LENGTH: 652
<212> TYPE: PRT
<213> ORGANISM: Artificial
<220> FEATURE:
<223> OTHER INFORMATION: hAxl-hFc

<400> SEQUENCE: 11

Glu Glu Ser Pro Phe Val Gly Asn Pro Gly Asn Ile Thr Gly Ala Arg
 1               5                  10                  15

Gly Leu Thr Gly Thr Leu Arg Cys Gln Leu Gln Val Gln Gly Glu Pro
                20                  25                  30

Pro Glu Val His Trp Leu Arg Asp Gly Gln Ile Leu Glu Leu Ala Asp
            35                  40                  45

Ser Thr Gln Thr Gln Val Pro Leu Gly Glu Asp Glu Gln Asp Asp Trp
        50                  55                  60

Ile Val Val Ser Gln Leu Arg Ile Thr Ser Leu Gln Leu Ser Asp Thr
65                  70                  75                  80

Gly Gln Tyr Gln Cys Leu Val Phe Leu Gly His Gln Thr Phe Val Ser
                85                  90                  95

Gln Pro Gly Tyr Val Gly Leu Glu Gly Leu Pro Tyr Phe Leu Glu Glu
            100                 105                 110

Pro Glu Asp Arg Thr Val Ala Ala Asn Thr Pro Phe Asn Leu Ser Cys
        115                 120                 125

Gln Ala Gln Gly Pro Pro Glu Pro Val Asp Leu Leu Trp Leu Gln Asp
130                 135                 140

Ala Val Pro Leu Ala Thr Ala Pro Gly His Gly Pro Gln Arg Ser Leu
145                 150                 155                 160

His Val Pro Gly Leu Asn Lys Thr Ser Ser Phe Ser Cys Glu Ala His
                165                 170                 175

Asn Ala Lys Gly Val Thr Thr Ser Arg Thr Ala Thr Ile Thr Val Leu
            180                 185                 190

Pro Gln Gln Pro Arg Asn Leu His Leu Val Ser Arg Gln Pro Thr Glu
        195                 200                 205

Leu Glu Val Ala Trp Thr Pro Gly Leu Ser Gly Ile Tyr Pro Leu Thr
    210                 215                 220

His Cys Thr Leu Gln Ala Val Leu Ser Asn Asp Gly Met Gly Ile Gln
225                 230                 235                 240

Ala Gly Glu Pro Asp Pro Pro Glu Glu Pro Leu Thr Ser Gln Ala Ser
                245                 250                 255

Val Pro Pro His Gln Leu Arg Leu Gly Ser Leu His Pro His Thr Pro
            260                 265                 270

Tyr His Ile Arg Val Ala Cys Thr Ser Ser Gln Gly Pro Ser Ser Trp
        275                 280                 285

Thr His Trp Leu Pro Val Glu Thr Pro Glu Gly Val Pro Leu Gly Pro
    290                 295                 300
```

```
Pro Glu Asn Ile Ser Ala Thr Arg Asn Gly Ser Gln Ala Phe Val His
305                 310                 315                 320

Trp Gln Glu Pro Arg Ala Pro Leu Gln Gly Thr Leu Leu Gly Tyr Arg
            325                 330                 335

Leu Ala Tyr Gln Gly Gln Asp Thr Pro Glu Val Leu Met Asp Ile Gly
            340                 345                 350

Leu Arg Gln Glu Val Thr Leu Glu Leu Gln Gly Asp Gly Ser Val Ser
            355                 360                 365

Asn Leu Thr Val Cys Val Ala Ala Tyr Thr Ala Ala Gly Asp Gly Pro
            370                 375                 380

Trp Ser Leu Pro Val Pro Leu Glu Ala Trp Arg Pro Val Lys Glu Pro
385                 390                 395                 400

Ser Thr Pro Ala Phe Ser Trp Pro Asp Ile Glu Gly Arg Met Asp Pro
                405                 410                 415

Lys Ser Cys Asp Lys Thr His Thr Cys Pro Pro Cys Pro Ala Pro Glu
                420                 425                 430

Leu Leu Gly Gly Pro Ser Val Phe Leu Phe Pro Pro Lys Pro Lys Asp
            435                 440                 445

Thr Leu Met Ile Ser Arg Thr Pro Glu Val Thr Cys Val Val Val Asp
            450                 455                 460

Val Ser His Glu Asp Pro Glu Val Lys Phe Asn Trp Tyr Val Asp Gly
465                 470                 475                 480

Val Glu Val His Asn Ala Lys Thr Lys Pro Arg Glu Glu Gln Tyr Asn
                485                 490                 495

Ser Thr Tyr Arg Val Val Ser Val Leu Thr Val Leu His Gln Asp Trp
            500                 505                 510

Leu Asn Gly Lys Glu Tyr Lys Cys Lys Val Ser Asn Lys Ala Leu Pro
            515                 520                 525

Ala Pro Ile Glu Lys Thr Ile Ser Lys Ala Lys Gly Gln Pro Arg Glu
530                 535                 540

Pro Gln Val Tyr Thr Leu Pro Pro Ser Arg Asp Glu Leu Thr Lys Asn
545                 550                 555                 560

Gln Val Ser Leu Thr Cys Leu Val Lys Gly Phe Tyr Pro Ser Asp Ile
                565                 570                 575

Ala Val Glu Trp Glu Ser Asn Gly Gln Pro Glu Asn Asn Tyr Lys Thr
            580                 585                 590

Thr Pro Pro Val Leu Asp Ser Asp Gly Ser Phe Phe Leu Tyr Ser Lys
            595                 600                 605

Leu Thr Val Asp Lys Ser Arg Trp Gln Gln Gly Asn Val Phe Ser Cys
            610                 615                 620

Ser Val Met His Glu Ala Leu His Asn His Tyr Thr Gln Lys Ser Leu
625                 630                 635                 640

Ser Leu Ser Pro Gly Lys His His His His His His
                645                 650
```